(12) United States Patent
Iacoviello et al.

(10) Patent No.: US 10,898,131 B2
(45) Date of Patent: *Jan. 26, 2021

(54) SYSTEMS AND METHODS FOR TREATING A PSYCHIATRIC DISORDER

(71) Applicant: ICAHN SCHOOL OF MEDICINE AT MOUNT SINAI, New York, NY (US)

(72) Inventors: Brian M. Iacoviello, New York, NY (US); Dennis S. Charney, New York, NY (US)

(73) Assignee: ICAHN SCHOOL OF MEDICINE AT MOUNT SINAI, New York, NY (US)

(*) Notice: Subject to any disclaimer, the term of this patent is extended or adjusted under 35 U.S.C. 154(b) by 127 days.

This patent is subject to a terminal disclaimer.

(21) Appl. No.: 16/189,059

(22) Filed: Nov. 13, 2018

(65) Prior Publication Data

US 2019/0076087 A1  Mar. 14, 2019

Related U.S. Application Data

(63) Continuation of application No. 15/513,490, filed as application No. PCT/US2015/051791 on Sep. 23, 2015, now Pat. No. 10,123,737.

(Continued)

(51) Int. Cl.
*A61B 5/00* (2006.01)
*A61B 5/16* (2006.01)
(Continued)

(52) U.S. Cl.
CPC ............ *A61B 5/4836* (2013.01); *A61B 5/00* (2013.01); *A61B 5/165* (2013.01); *A61B 5/167* (2013.01);
(Continued)

(58) Field of Classification Search
CPC .......... A61B 5/00; A61B 5/165; A61B 5/167; A61B 5/4076; A61B 5/4836; G06F 19/00; G16H 20/70
See application file for complete search history.

(56) References Cited

U.S. PATENT DOCUMENTS 5,678,571 A  10/1997 Brown
5,736,986 A   4/1998 Sever, Jr.
(Continued)

FOREIGN PATENT DOCUMENTS

| JP | 2007-044311 | 2/2007 |
| JP | 2010-512802 | 4/2010 |
| WO | WO-2008/064431 | 6/2008 |

OTHER PUBLICATIONS

Extended European Search Report dated May 2, 2018 for EP 15844330.9, 9 pages.
(Continued)

*Primary Examiner* — George Manuel
(74) *Attorney, Agent, or Firm* — Foley & Lardner LLP

(57) ABSTRACT

Systems and methods for treating a subject with a psychiatric disorder are provided in which a therapy session is conducted. In the therapy session, each respective expression image in a plurality of expression images is sequentially displayed. Each expression image is independently associated with an expression. The successive display of images is construed as a tiled series of expression image subsets, each consisting of N expression images. Upon completion of the display of each respective subset, the user is challenged as to whether the first and the last images in the respective subset exhibit the same emotion. A score is determined for the respective subset based on whether the subject learned to respond correctly. The number of images in each subset is adjusted to a new number based on these scores. A treatment (Continued)

regimen is prescribed to the subject for the psychiatric disorder based at least in part on the scores.

70 Claims, 7 Drawing Sheets

Related U.S. Application Data

(60) Provisional application No. 62/054,371, filed on Sep. 23, 2014.

(51) Int. Cl.
 *G16H 20/70* (2018.01)
 *G06F 19/00* (2018.01)

(52) U.S. Cl.
 CPC ............ *A61B 5/4076* (2013.01); *G06F 19/00* (2013.01); *G16H 20/70* (2018.01)

(56) References Cited

U.S. PATENT DOCUMENTS

| | | | |
|---|---|---|---|
| 5,836,819 A | 11/1998 | Ugawa | |
| 5,913,310 A | 6/1999 | Brown | |
| 5,918,603 A | 7/1999 | Brown | |
| 5,964,700 A | 10/1999 | Tallman et al. | |
| 6,057,846 A | 5/2000 | Sever, Jr. | |
| 6,165,126 A | 12/2000 | Merzenich et al. | |
| 6,167,311 A | 12/2000 | Rezai | |
| 6,186,145 B1 | 2/2001 | Brown | |
| 6,273,027 B1 | 8/2001 | Watson et al. | |
| 6,322,503 B1 | 11/2001 | Sparhawk, Jr. | |
| 6,425,764 B1 | 7/2002 | Lamson | |
| 6,495,601 B1 | 12/2002 | Hochman | |
| 6,622,047 B2 | 9/2003 | Barrett et al. | |
| 6,652,470 B2 | 11/2003 | Patton et al. | |
| 6,708,064 B2 | 3/2004 | Rezai | |
| 6,746,409 B2 | 6/2004 | Keirsbilck et al. | |
| 6,996,261 B2 | 2/2006 | Decharms | |
| 7,013,177 B1 | 3/2006 | Whitehurst et al. | |
| 7,122,004 B1 | 10/2006 | Cassily | |
| 7,187,790 B2 | 3/2007 | Sabol et al. | |
| 7,313,442 B2 | 12/2007 | Velasco et al. | |
| 7,346,395 B2 | 3/2008 | Lozano et al. | |
| 7,353,065 B2 | 4/2008 | Morrell | |
| 7,490,085 B2 | 2/2009 | Walker et al. | |
| 7,603,174 B2 | 10/2009 | De Ridder | |
| 7,652,665 B2 | 1/2010 | Fukushima et al. | |
| 7,877,147 B2 | 1/2011 | Shalev et al. | |
| 7,901,211 B2 | 3/2011 | Pennebaker | |
| 7,942,816 B2 | 5/2011 | Satoh et al. | |
| 7,973,043 B2 | 7/2011 | Migaly | |
| 8,069,125 B2 | 11/2011 | Jung et al. | |
| 8,306,635 B2 | 11/2012 | Pryor | |
| 8,500,635 B2 | 8/2013 | Zilca et al. | |
| 8,566,121 B2 | 10/2013 | Ramasubramanian et al. | |
| 8,843,210 B2 | 9/2014 | Simon et al. | |
| 8,940,308 B2 | 1/2015 | Turkel et al. | |
| 9,308,445 B2 | 4/2016 | Merzenich et al. | |
| 9,308,446 B1 | 4/2016 | Merzenich et al. | |
| 9,440,090 B2 | 9/2016 | Jo et al. | |
| 9,463,132 B2 | 10/2016 | Simmons | |
| 9,601,026 B1 | 3/2017 | Merzenich et al. | |
| 9,821,167 B2 | 11/2017 | Carcieri et al. | |
| 9,886,866 B2 | 2/2018 | Merzenich et al. | |
| 9,997,082 B2 | 6/2018 | Kaleal | |
| 10,002,544 B2 | 6/2018 | Merzenich et al. | |
| 2008/0039737 A1* | 2/2008 | Breiter | A61B 5/0484 600/544 |
| 2008/0045780 A1 | 2/2008 | Brown | |
| 2009/0018407 A1 | 1/2009 | Jung et al. | |
| 2011/0027765 A1 | 2/2011 | Nader | |
| 2013/0090562 A1 | 4/2013 | Ryan | |
| 2013/0102918 A1 | 4/2013 | Etkin et al. | |
| 2016/0023099 A1 | 1/2016 | Tymoszczuk | |

OTHER PUBLICATIONS

International Search Report and Written Opinion dated Jan. 17, 2016 for PCT/US2015/051791 7 pages.
Notice of Allowance on U.S. Appl. No. 15/513,490 dated Sep. 19, 2018.
U.S. Office Action on U.S. Appl. No. 15/513,490 dated Jun. 1, 2018.
First Examination Report on AU 2015320698 dated Nov. 4, 2019.
Notice of Refusal on JP 2017-535634 dated Jun. 16, 2020.
Notice of Refusal on JP 2017-535634 dated Aug. 6, 2019.

* cited by examiner

300

```
┌─────────────────────────────────────────────────────────────────────────┐
│ Conduct an initial assessment of the subject prior to the conducting the therapy in    │─302
│ order to select the therapy session from among a plurality of therapy session          │
│                          treatment protocols.                                          │
└─────────────────────────────────────────────────────────────────────────┘
                                         ↓
┌─────────────────────────────────────────────────────────────────────────┐
│ Sequentially display each respective expression image in a plurality of expression      │
│   images for a predetermined amount of time and each expression image in the           │─304
│  plurality of expression images is independently associated with an expression in a    │
│                              set of expressions.                                       │
│                                                                                         │
│   ┌─────────────────────────────────────────────────────────────────┐                  │
│   │  The set of expressions comprises four or more different expressions (e.g., │─306   │
│   │                     happy, worried, angry and sad).             │                  │
│   └─────────────────────────────────────────────────────────────────┘                  │
│                                                                                         │
│   ┌─────────────────────────────────────────────────────────────────┐                  │
│   │ The predetermined amount of time a particular expression image is displayed │      │
│   │   is random and independent of the amount of time any other image is        │─308   │
│   │                              displayed.                                     │      │
│   └─────────────────────────────────────────────────────────────────┘                  │
│                                                                                         │
│   ┌─────────────────────────────────────────────────────────────────┐                  │
│   │   The amount of time between the display of any two consecutive images is   │      │
│   │   random and independent of the amount of time between the display of any   │─310   │
│   │                        two other consecutive images.                        │      │
│   └─────────────────────────────────────────────────────────────────┘                  │
└─────────────────────────────────────────────────────────────────────────┘
                                         ↓
┌─────────────────────────────────────────────────────────────────────────┐
│   Responsive to completion of each respective expression image subset within the       │
│  plurality of expression images, receive a response from the subject to a query as to  │
│  whether the first and the last expression image in the respective expression image    │
│   subset exhibits the same emotion, and wherein each respective expression image       │─312
│    subset within the plurality of expression images consists of N sequentially         │
│               displayed expression images, wherein N is a predetermined integer.       │
│                                                                                         │
│   ┌─────────────────────────────────────────────────────────────────┐                  │
│   │   The respective expression image subsets are overlapping, wherein each     │─314   │
│   │   subset overlaps by N-1 images with another respective image subset.       │      │
│   └─────────────────────────────────────────────────────────────────┘                  │
│                                                                                         │
│   ┌─────────────────────────────────────────────────────────────────┐                  │
│   │         There are ten to twenty respective expression image subsets.        │─316   │
│   └─────────────────────────────────────────────────────────────────┘                  │
└─────────────────────────────────────────────────────────────────────────┘
                                         ↓
```

Figure 3A

SYSTEMS AND METHODS FOR TREATING A PSYCHIATRIC DISORDER

CROSS REFERENCE TO RELATED APPLICATIONS

The present application claims priority to and is a continuation of U.S. patent application Ser. No. 15/513,490, filed Mar. 22, 2017, entitled "SYSTEMS AND METHODS FOR TREATING A PSYCHIATRIC DISORDER," which in turn is a national stage application, filed under 35 U.S.C. § 371, of PCT Application No. PCT/US2015/051791, filed Sep. 23, 2015, entitled "SYSTEMS AND METHODS FOR TREATING A PSYCHIATRIC DISORDER," which claims priority to U.S. Provisional Application No. 62/054,371, entitled "SYSTEMS AND METHODS FOR TREATING A PSYCHIATRIC DISORDER," filed Sep. 23, 2014, all of which are hereby incorporated by reference in their entireties.

STATEMENT REGARDING FEDERALLY SPONSORED RESEARCH OR DEVELOPMENT

This invention was made with government support under 1K23MH099223-01A1 awarded by The National Institute of Health. The government has certain rights in the invention.

TECHNICAL FIELD

The present invention relates generally to psychiatric disorder treatments. More particularly, the invention is directed to treatments relating to affective disorders (AD).

BACKGROUND

There is an urgent need for more effective treatments for psychiatric disorders characterized by negative affect (Affective Disorders or ADs), such as major depressive disorder (MDD), post-traumatic stress disorder (PTSD), and anxiety disorders. Such ADs are common, disabling and costly. Indeed, an estimated 350 million people worldwide suffer from depression, which is the leading cause of disability in Americans ages 15-44. Novel interventions are needed as available therapies precipitate remission in only one third of subjects.

SUMMARY

Psychiatric disorders, including affective disorders (ADs), can be treated by neurobehavioral therapies (NBTs) that stimulate the network of brain regions implicated in these disorders. In particular, cognitive emotional exercises can enhance cognitive control of emotional information-processing that simultaneously activates brain regions (e.g., the dorsolateral PFC (DLPFC) and amygdala) that are impaired in such ADs. Without being bound by any particular theory of operation or mechanism, it is believed that exercising the ability to manipulate emotional information in working memory by performing such cognitive emotional exercises enhances cognitive control for emotional material and emotion regulation, and has antidepressant effects.

In one aspect, provided herein is a computing system for the treatment of a psychiatric disorder. The computing system includes one or more processors, memory, and one or more programs. The one or more programs are stored in the memory and are configured to be executed by the one or more processors to treat a subject in need of treatment of a psychiatric disorder. The one or more programs include instructions for conducting a therapy session and prescribing a treatment regimen to the subject for the psychiatric disorder. The therapy session comprises sequentially displaying each respective expression image in a plurality of expression images for a predetermined amount of time. Each expression image in the plurality of expression images is images is (i) independently associated with a respective expression in a set of expressions and (ii) engineered to display a predetermined intensity of the respective expression on an intensity scale that ranges from low intensity to high intensity of the respective expression. In other words, expression images are engineered to display a certain intensity of the expression (e.g., level 1 includes expression images with 90% intensity, level 2 includes expression images with 80% intensity, level 3 includes expression images with 70% intensity, level 4 includes expression images with 60% intensity, and level 5 includes expression images with 50% emotion intensity in the images). This contributes to the difficulty of the task across levels. This is purposeful to increase engagement and learning throughout the session.

Although each expression image is independently displayed a sliding window of the last N expression images is termed an "expression image subset." As such, by the time all of the expression images have been displayed, a plurality of expression image subsets has necessarily been displayed. Accordingly, in the therapy session, responsive to completion (e.g. display) of the expression images in a respective expression image subset within the plurality of expression images, a response from the subject to a query as to whether the first and the last expression image in the respective expression image subset exhibits the same emotion is received. In other words, after each expression image subset is displayed, the subject is challenged as to whether the first and last expression image in the expression image subset connotes the same expression. Each respective expression image subset within the plurality of expression images consists of N sequentially displayed expression images. The value N is a predetermined integer the value of which is determined by the stage in the therapy session the subject has achieved. In the therapy session, a score is determined for each respective expression image subset within the plurality of expression image subsets based at least in part upon (a) the response to the query for the respective expression image subset, (b) the expression associated with the first expression image in the respective expression image subset, and (c) the expression associated with the last expression image in the respective expression image subset. In this way a plurality of scores is determined. The therapy session continues by resetting the value of N to a new positive integer value based at least in part on the plurality of scores. In some optional embodiments, the therapy session continues by prescribing a treatment regimen to the subject based at least in part on the reset value of N or some other aspect of the above identified scoring process.

In some embodiments, the psychiatric disorder is an affective disorder (AD). In certain embodiments, the AD is major depressive disorder (MDD), bipolar disorder, post traumatic stress disorder (PTSD), general anxiety disorder, social phobia, obsessive compulsive disorder, treatment resistant depression, or borderline personality disorder. In particular embodiments, the affective disorder is MDD.

In some embodiments, the sequentially displaying, receiving, determining, and resetting are repeated a plurality of times in the therapy session. In certain embodiments, the sequentially displaying, receiving, determining, and resetting are repeated 10 to 20 times during a therapy session.

In some embodiments, the value of N prior to the initial resetting is one, two, three, four, five, six, seven, eight, nine or ten. In particular embodiments, the value of N prior to the initial resetting is two.

In some embodiments, there are ten to twenty respective expression image subsets. In particular embodiments, there are twenty respective expression image subsets.

In some embodiments, the respective expression image subsets are overlapping. In certain embodiments, the expression image subsets overlap by N−1 images with another respective image subset.

In some embodiments of the computing system, the set of expressions include happy, worried, angry and sad. In some embodiments, there are two, three, four or five different expression images that are independently associated with each expression in the set of expressions.

In some embodiments, the therapy session is repeated on a recurring basis over the course of a number of weeks. In some embodiments, the therapy session is repeated on a recurring basis over the course of a number of weeks prior to prescribing a treatment regimen to the subject. In certain embodiments the therapy session is repeated two to ten times over the course of a number of weeks prior to the prescribing.

In some embodiments, the treatment regimen is characterized by a frequency by which the therapy session is conducted as well as an absolute number of times the therapy sessions are conducted.

In some embodiments, the treatment regimen is characterized by a frequency by which the therapy session is conducted as well as an absolute number of times the therapy sessions are conducted and furthermore is characterized by the use of a pharmaceutical composition. In some embodiments, the affective disorder is MDD and the pharmaceutical composition is a selective serotonin reuptake inhibitor (SSRI), a serotonin norepinephrine reuptake inhibitor (SNRI), a cognitive enhancer, ketamine or ketamine derivative or combinations thereof. In some embodiments, the affective disorder is post traumatic stress disorder (PTSD) and the pharmaceutical composition is an SSRI, an SNRI, a cognitive enhancer or combinations thereof. In some embodiments, the affective disorder is general anxiety disorder and the pharmaceutical composition is an SSRI, an SNRI, a cognitive enhancer, ketamine or a ketamine derivative or combinations thereof. In some embodiments, the affective disorder is social phobia and the pharmaceutical composition is an SSRI, an SNRI, a cognitive enhancer or combinations thereof. In some embodiments, the affective disorder is obsessive compulsive disorder and the pharmaceutical composition is an SSRI, a cognitive enhancer or combinations thereof. In some embodiments, the affective disorder is borderline personality disorder and the pharmaceutical composition is an SSRI, an SNRI, ketamine or a ketamine derivative, a cognitive enhancer or combinations thereof.

In some embodiments, the treatment regimen is characterized by a frequency by therapy session the therapy session is conducted as well as an absolute number of times the therapy session is conducted and furthermore is characterized by the use of a brain stimulation intervention. In certain embodiments, the brain stimulation intervention stimulates the dorsal lateral prefrontal cortex (DLPFC). In certain embodiments, the brain stimulation intervention is transcranial direct current stimulation.

In some embodiments, the treatment regimen is characterized by a frequency by which the therapy session is conducted as well as an absolute number of times the therapy session is conducted and furthermore is characterized by the use of a psychotherapy for an affective disorder. In certain embodiments, the psychotherapy is an empirically supported psychotherapy for an affective disorder. In certain embodiments, the psychotherapy is a cognitive behavioral psychotherapy.

In some embodiments, the predetermined amount of time that respective images are displayed is less than ten seconds. In some embodiments, the predetermined amount of time that respective images are displayed is between 0.2 seconds and 10 seconds.

In some embodiments, each expression image in the plurality of expression images is grey scaled. In other embodiments, each expression image in the plurality of expression images is in color. In yet other embodiments, the plurality of expression images includes color and grey scaled expression images.

In some embodiments, the prescribing comprises communicating the score to a remote server for evaluation by a prescribing clinician.

In some embodiments, the sequentially displaying comprises retrieving the plurality of expression images from a database that stores the plurality of expression images. Such a database stores, for each respective expression image in the plurality of expression images, the emotion associated with the respective expression image.

In some embodiments, the plurality of scores is determined as the total number of correct responses from the subject to the query as to whether the first and last expression in a respective expression image subset is the same. In certain embodiments, the resetting of N is based at least in part on the percentage of correct responses from the subject to the query as compared to the total number of response. In some embodiments, N is reset to N+Y if the percentage of correct responses is greater than a first threshold percentage, N is reset to N−Y if the percentage of correct responses is less than a second threshold percentage and N does not reset if the percentage of correct responses is between the first and second threshold percentage. In some embodiments, Y is the value 1. In some embodiments, the value of Y is an integer value that is determined by the size of N. For instance, in one embodiment, if N is five or less, Y is 1, whereas if N is six or greater, Y is 2.

In some embodiments an initial assessment of the subject is held prior to conducting the therapy session in order to select the appropriate therapy session treatment protocol from among a plurality of therapy session treatment protocols. In certain embodiments, the initial assessment includes obtaining information regarding the cognitive functioning and/or the emotional functioning of the subject.

In some embodiments, the prescribing of the treatment regimen is further based at least in part on the cognitive functioning and emotional functioning of the subject after the training session. In some embodiments, the subject is assessed after conducting the therapy. In such embodiments, this assessment is used as the basis, at least in part, for the prescribing a treatment regimen to the subject. In particular embodiments, the assessment is of the cognitive function and/or emotional function of the subject.

In some embodiments, the subject is provided with a performance evaluation based at least in part on the score determined for a respective expression image subset in the therapy session. In some embodiments, the subject is provided with a performance evaluation based at least in part on the plurality of scores of a therapy session. In some embodiments, the subject is provided with a performance evaluation based at least in part on the plurality of scores of a plurality of therapy sessions.

In some embodiments, the therapy session is repeated on a recurring basis over the course of a number of weeks prior to prescribing a treatment regimen to the subject, and furthermore, the subject is intermittently evaluated for the presence of one or more symptoms of the psychiatric disorder to be treated. In certain embodiments, this intermittent evaluation for the presence of one or more symptoms of the psychiatric disorder to be treated includes a patient health questionnaire (PHQ) check (e.g., PHQ-2, PHQ-9, PHQ-15, GAD-7, etc.).

The computing system of any one of claims 1-35, wherein at least one expression image in the plurality of expression images is not a facial expression.

The computing system of any one of claims 1-35, wherein each expression image in the plurality of expression images is not a facial expression.

The computing system of any one of claims 1-35, wherein at least one expression image in the plurality of expression images is a facial expression.

The computing system of any one of claims 1-35, wherein each expression image in the plurality of expression images is a facial expression.

In some embodiments, the predetermined intensity of the respective expression on the intensity scale of respective displayed expression images increases from the low intensity to the high intensity across the therapy session. In some embodiments, the therapy session reduces the depression symptoms of the subject by at least 10%, at least 20%, at least 30%, at least 40%, at least 50%, at least 60%, or at least 70%.

In some embodiments, at least one expression image in the plurality of expression images is not a facial expression. In some embodiments, each expression image in the plurality of expression images is not a facial expression. In some embodiments at least one expression image in the plurality of expression images is a facial expression. In some embodiments each expression image in the plurality of expression images is a facial expression.

BRIEF DESCRIPTION OF THE DRAWINGS

For a better understanding of the aforementioned implementations of the invention as well as additional implementations thereof, reference should be made to the Description of Implementations below, in conjunction with the following drawings in which like reference numerals refer to corresponding parts throughout the figures.

FIGS. 3A-3C are flow charts of a method for treating a psychiatric disorder, according to some embodiments.

Reference will now be made in detail to implementations, examples of which are illustrated in the accompanying drawings. In the following detailed description, numerous specific details are set forth in order to provide a thorough understanding of the present invention. However, it will be apparent to one of ordinary skill in the art that the present invention may be practiced without these specific details.

DESCRIPTION OF IMPLEMENTATIONS

The implementations described herein provide various technical solutions to improve the health of human subjects having a psychiatric disorder by providing a treatment for a psychiatric disorder. Details of implementations are now described in relation to the Figures.

Figure 1:
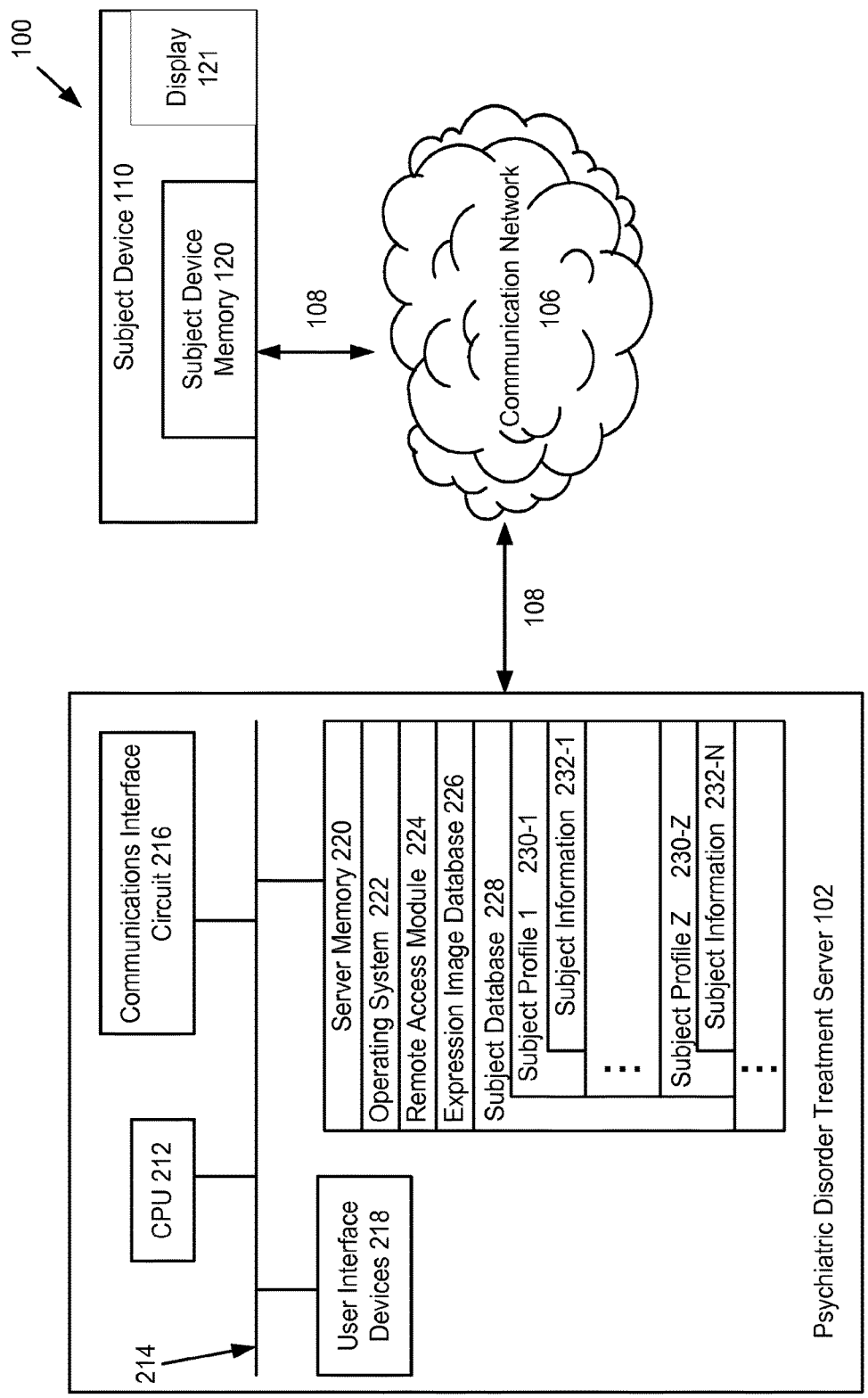
FIG. 1 is a block diagram of an electronic network for providing a treatment for a subject in need of treatment of a psychiatric disorder, according to some embodiments.

FIG. 1 is a diagrammatic view of an electronic network 100 for the treatment of a psychiatric disorder in accordance with some embodiments. The network 100 comprises a series of points or nodes interconnected by communication paths. The network 100 may interconnect with other networks, may contain subnetworks, and may be embodied by way of a local area network (LAN), a metropolitan area network (MAN), a wide area network (WAN), or a global network (the Internet). In addition, the network 100 may be characterized by the type of protocols used on it, such as WAP (Wireless Application Protocol), TCP/IP (Transmission Control Protocol/Internet Protocol), NetBEUI (NetBIOS Extended User Interface), or IPX/SPX (Internetwork Packet Exchange/Sequenced Packet Exchange). Additionally, the network 100 may be characterized by whether it carries voice, data, or both kinds of signals; by who can use the network 100 (whether it is public or private); and by the usual nature of its connections (e.g. dial-up, dedicated, switched, non-switched, or virtual connections).

The network 100 connects a plurality of subject devices 110 to at least one psychiatric disorder treatment server 102. This connection is made via a communication or electronic network 106 that may comprise an Intranet, wireless network, cellular data network or preferably the Internet. The connection is made via communication links 108, which may, for example, be coaxial cable, copper wire (including, but not limited to, PSTN, ISDN, and DSL), optical fiber, wireless, microwave, or satellite links. Communication between the devices and servers preferably occurs via Internet protocol (IP) or an optionally secure synchronization protocol, but may alternatively occur via electronic mail (email).

The psychiatric disorder treatment server 102 is shown in FIG. 1, and is described below as being distinct from the subject devices 110. The psychiatric disorder treatment server 102 comprises at least one data processor or central processing unit (CPU) 212, a server memory 220, (optional) user interface devices 218, a communications interface circuit 216, and at least one bus 214 that interconnects these elements. The server memory 220 includes an operating system 222 that stores instructions for communicating, processing data, accessing data, storing data, searching data, etc. The server memory 220 also includes remote access module 224 and an expression image library (database) 226. In some embodiments, the remote access module 224 is used for communicating (transmitting and receiving) data between the psychiatric disorder treatment server 102 and the communication network 106. In some embodiments, the expression image database 226 is used to store expression images that can be used by one or more programs of the computing system provided herein (e.g., programs for conducting a therapy session).

In certain embodiments, the server memory 220 further includes a subject database 228 preferably containing a plurality of subject profiles 230-1 to 230-Z. In some embodiments, each subject profile 230-1 to 230-Z contains subject information 232, such as, but not limited to, performance scores of the therapy sessions described herein, pre and post therapy session assessments, and/or therapy session histories. In certain embodiments, the subject profile 230 further includes subject contact details, information concerning the subject's medical history, the subject's medical insurance details, etc. In some embodiments, the subject database 228 also comprises information regarding psychiatric disorder treatment plans such as, but not limited to, the frequency of conducting therapy sessions describe herein, the absolute number of times that the therapy sessions are conducted, and/or any pharmaceuticals prescribed or other treatments (e.g., medication and other psychotherapies that target the brain regions and neural networks related to the psychiatric disorder being treated) administered concurrently with the treatments provided herein.

In some embodiments, a subject device 110 is a device used by a subject in need of treatment of a psychiatric disorder as described herein. The subject device 110 accesses the communication network 106 via remote client computing devices, such as desktop computers, laptop computers, notebook computers, handheld computers, tablet computers, smart phones, or the like. In some embodiments, the subject device 110 includes a data processor or central processing unit (CPU), a user interface device, communications interface circuits, and buses, similar to those described in relation to the psychiatric disorder treatment server 102. In some embodiments, the subject device 110 includes a display 121 for displaying expression images as described below. The subject device 110 also includes memories 120, described below. Memories 220 and 120 may include both volatile memory, such as random access memory (RAM), and non-volatile memory, such as a hard-disk or flash memory.

Figure 2:
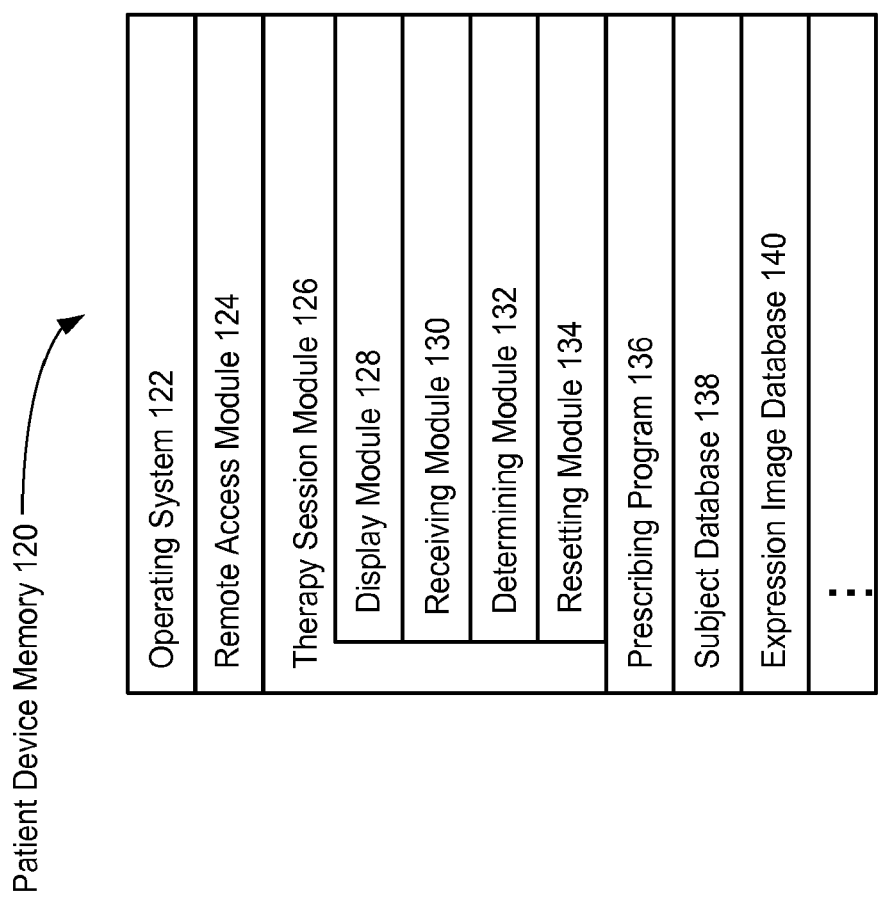
FIG. 2 is a block diagram of the subject device memory shown in FIG. 1, according to some embodiments.

FIG. 2 is a block diagram of a subject device memory 120 shown in FIG. 1, according to some embodiments. The subject device memory 120 includes an operating system 122 and remote access module 124 compatible with the remote access module 224 (FIG. 1) in the server memory 220 (FIG. 1).

In some embodiments, the subject device memory 120 includes a therapy session module 126. The therapy session module 126 includes instructions for conducting a therapy program, as detailed below. In some embodiments, the therapy session module 126 comprises one or more modules for conducting a therapy session. For instance, in some embodiments, the therapy session module 126 included in the subject device memory 120 comprises a display module 128, a receiving module 130, a determination module 132, and a resetting module 134.

In some embodiments, the subject memory device memory 120 includes a prescribing program 136, wherein the prescribing program 136 contains instructions to prescribe a treatment regimen to the subject undergoing the treatment described herein. In some embodiments, the prescribing is based at least in part on results generated by the therapy session program 126 (e.g., the reset value of N, as discussed in detail below).

In some embodiments, the subject device memory 120 also comprises a subject database 138 that stores data relating to the subject using the subject device 110. In some embodiments, the subject database 138 stores data relating to user subject's performance scores for a therapy session or plurality of therapy sessions as described herein, pre and post therapy session assessments, and/or therapy session histories. In some embodiments, the subject database 138 also stores data relating to the subject's psychiatric disorder treatment plan such as, but not limited to, the frequency of conducting a therapy session describe herein, the absolute number of times that therapy sessions are conducted, and/or any pharmaceuticals prescribed or other treatments (e.g., medication and other psychotherapies that target the brain regions and neural networks related to the psychiatric disorder being treated) administered concurrently with the treatments provided herein.

In some embodiments, the subject device memory 120 also comprises an expression image database 140. In certain embodiments, the expression image database comprises expression images that are used in the therapy session of the computing system as described below.

It should be noted that the various databases described above have their data organized in a manner so that their contents can easily be accessed, managed, and updated. The databases may, for example, comprise flat-file databases (a database that takes the form of a table, where only one table can be used for each database), relational databases (a tabular database in which data is defined so that it can be reorganized and accessed in a number of different ways), or object-oriented databases (a database that is congruent, with the data defined in object classes and subclasses). The databases may be hosted on a single server or distributed over multiple servers. In some embodiments, there is an expression image database 226 but no expression image database 140.

Figure 3B:
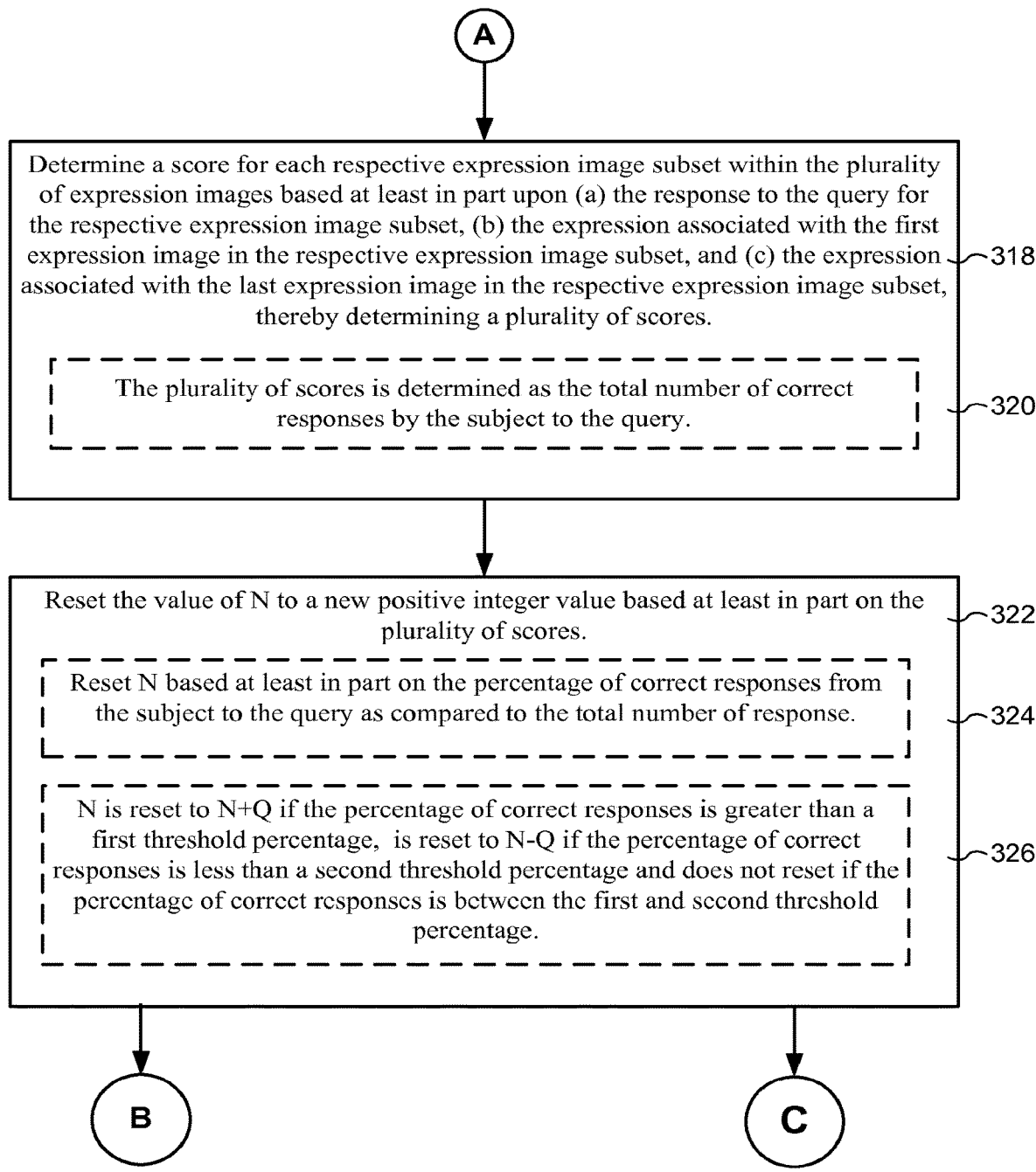
Figure 3C:
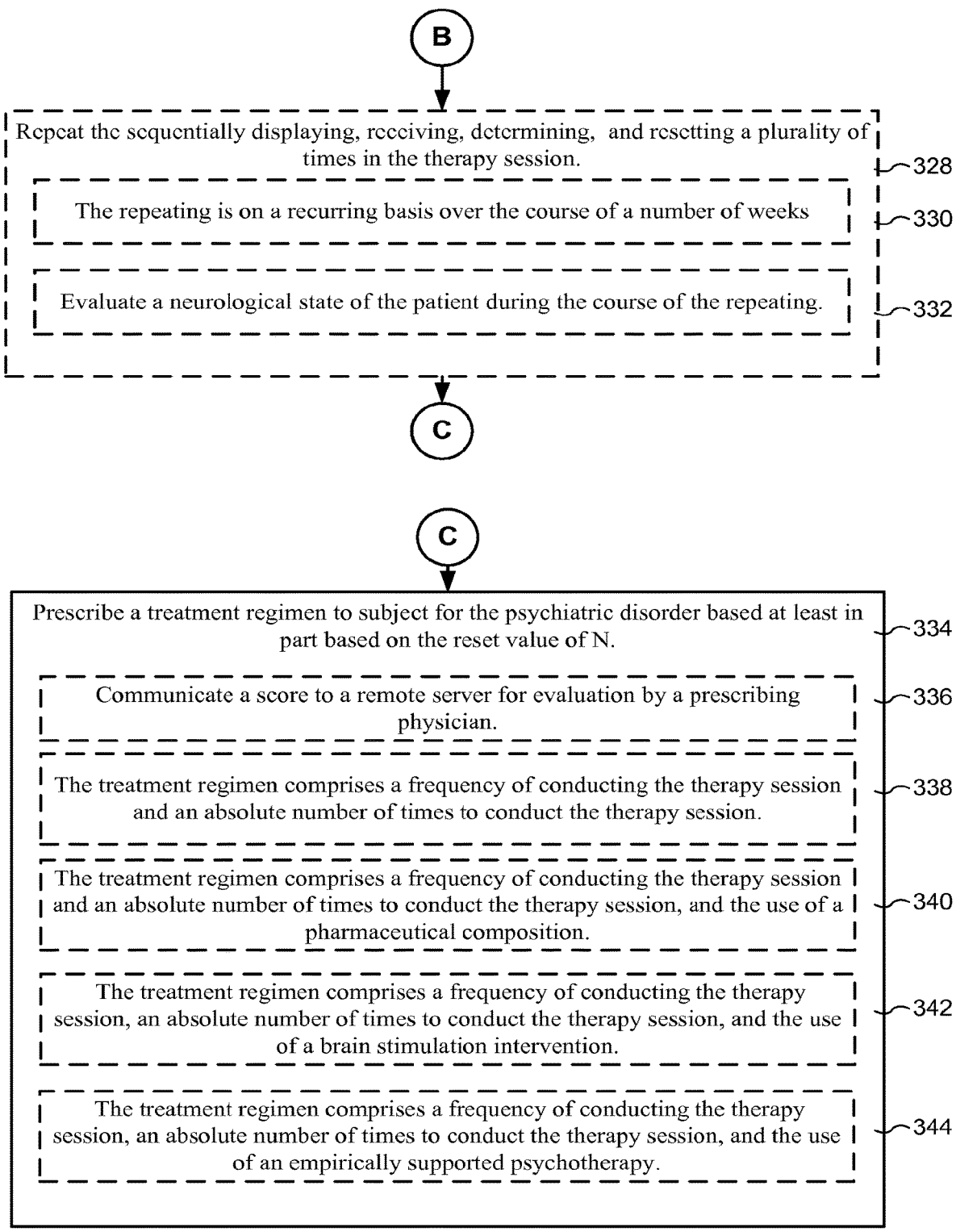

FIGS. 3A-C are flow charts that illustrate the method 300 for the treatment of a psychiatric disease, according to some embodiments of the subject computing system. In some embodiments, the method is carried out by one or more programs of the subject computer system described herein.

In some embodiments, the method is for the treatment of an affective disorder (AD). As used herein, an "affective disorder" refers to a psychological disorders characterized by abnormalities of emotional state (i.e., a mood disorder). Examples of affective disorders include, but are not limited to: attention-deficit hyperactivity disorder, bipolar disorder, body dysmorphic disorder, bulimia nervosa and other eating disorders, cataplexyy, dysthymia, general anxiety disorder, hypersexuality, irritable bowel syndrome impulse-control disorders, kleptomania, migraine, major depressive disorder, narcolepsy, obsessive-compulsive disorder, oppositional-defiant disorder, panic disorder, posttraumatic stress disorder, premenstrual dysphoric disorder, treatment resistant depression, and social anxiety disorder. In certain embodiments, the subject systems and methods described herein are for the treatment of an affective disorder chosen from major depressive disorder (MDD), post traumatic stress disorder (PTSD), general anxiety disorder, social phobia, obsessive compulsive disorder, treatment resistant depression and borderline personality disorder. In particular embodiments, the subject system and methods described herein are for the treatment of MDD.

In some embodiments, the subject method comprises A) conducting a therapy session 302-326 and B) prescribing a treatment regimen 334 to the subject for the psychiatric disorder. The conducting the therapy session includes sequentially displaying (304) each respective expression image in a plurality of expression images for a predetermined amount of time, where each expression image in the plurality of expression images is independently associated with an expression in a set of expressions. This sequential display of expression images can be thought of as the sequential display of expression image subsets in a plurality of expression image subsets, where each expression image subset consists of the last N displayed expression image subsets. For instance, in some embodiments, the expression image subsets are tiled with respect to each other, such that they each overlap with a temporally neighboring expression image by one expression image.

In some embodiments, the set of expressions invoked by the plurality of expression images comprises four or more different expressions (e.g., happy, worried, angry and sad) (306). In some embodiments, the predetermined amount of time a particular expression image is displayed is random and independent of the amount of time any other image is displayed (308). In some embodiments, the amount of time between the display of any two consecutive expression images is random and independent of the amount of time between the display of any two other consecutive images (310).

In a therapy session, the subject is queried at the completion of each respective expression image subset within the plurality of expression images as to whether the emotion of the first and last expression image in the respective image subset is the same (312). For instance, the user presses a first key (e.g., "1") if the expressions are the same and a second key (e.g., "2") if the expressions are different. Because the respective expression image subsets are temporarily tiled, this equates in some embodiments to querying the subject after each expression image once the first expression image subset has been displayed. As such, responsive to completion of each respective expression image subset, a response from the subject to a query as to whether the first and the last expression image in the respective expression image subset exhibits the same emotion is received. In such embodiments, each respective expression image subset within the plurality of expression images consists of N sequentially displayed expression images, where N is a predetermined integer (e.g., 2, 3, 4, 5, 6, 7, 8, 9, or greater). In some embodiments, the respective expression image subsets are overlapping, where each subset (temporally) overlaps by N−1 images with another respective image subset, where N is the number of expression images in each respective image subset. In some embodiments, the respective expression image subsets are overlapping, where each subset (temporally) overlaps by N−2 images with another respective image subset. In some embodiments, the respective expression image subsets are overlapping, where each subset (temporally) overlaps by N−3 images with another respective image subset. In some embodiments, the respective expression image subsets are overlapping, where each subset (temporally) overlaps by N−Y images with another respective image subset, where N is the number of images in each respective image subset and Y is an integer less than N.

In some embodiments, there are ten to twenty respective expression image subsets in the plurality of expression images (316). In some embodiments, there are between three and one hundred respective expression image subsets in the plurality of expression images. In some embodiments, there are between three to fifty respective expression image subsets in the plurality of expression images. In some embodiments, there are between three to thirty respective expression image subsets in the plurality of expression images.

The therapy session continues with the determination of a score for each respective expression image subset within the plurality of expression images based at least in part upon (a) the response to the query for the respective expression image subset, (b) the expression associated with the first expression image in the respective expression image subset, and (c) the expression associated with the last expression image in the respective expression image subset, thereby determining a plurality of scores (318). In some embodiments, the plurality of scores is determined as the total number of correct responses by the subject to the query (320).

The therapy session continues by resetting the value of N to a new positive integer value based at least in part on the plurality of scores (322). In some embodiments, resetting of the positive integer N is based at least in part on the percentage of correct responses from the subject to the query as compared to the total number of response (324). In some embodiments, N is reset to N+Q if the percentage of correct responses is greater than a first threshold percentage, is reset to N−Q if the percentage of correct responses is less than a second threshold percentage and does not reset if the percentage of correct responses is between the first and second threshold percentage. Typically, Q if the value "1", though other values are possible (e.g., 2, 3, 4, or any value less than N).

In some embodiments, a treatment regimen is prescribed based at least in part on the reset value of N (334).

Now that an overview of a therapy session has been detailed, some specific embodiments will be described. In some embodiments, a therapy session (e.g., as disclosed in steps 302-326) comprises a first step of: i) sequentially displaying 304 each respective expression image in a plurality of expression images for a predetermined amount of time, where each expression image in the plurality of expression images is independently associated with an expression in a set of expressions. In certain embodiments of the computing system provided herein, the sequentially displaying is performed according to instructions included in a display module 128 stored in the subject device memory 120 of a subject device 110.

In some embodiments, the sequentially displaying comprises retrieving a plurality of expression images from a database that stores expression images (e.g., an expression image database 140 and 226). In some embodiments, the expression image database further stores the emotion associated with each expression image stored in the database. In certain embodiments, the database that stores expression images is included in the server memory 220 of the psychiatric disorder treatment server 102. In other embodiments, the database that stores expression images is located in the subject device memory 120 of the subject device 110.

In some embodiments, after the retrieval of a plurality of expression images from the expression image database 140 or 226, the images are sequentially displayed to the subject on a display 121 of the subject device 110. In certain embodiments, the predetermined amount of time that each particular expression image in the plurality of expression images is displayed is between 0.1 and 5.0 seconds. In certain embodiments, the predetermined amount of time that each particular expression image in the plurality of expression images is displayed is between 0.5 and 3.5 seconds. In certain embodiments, all of the expression images are sequentially displayed for the same predetermined amount of time. In certain embodiments, each expression image in the plurality is displayed for a predetermined amount of time that is random and independent of the amount of time any other image is displayed (308). In some embodiments, the predetermined amount of time that a particular expression image is displayed is randomly chosen from a set of two to ten predetermined lengths of time. In some embodiments, the amount of time between the display of two consecutive images is between 0.1 and 5.0 seconds. In certain embodiments, the amount of time between the display of two consecutive images is between 0.75 and 3.5 seconds. In certain embodiments, the amount of time between the display of two consecutive images is the same for all consecutive images sequentially displayed. In other embodiments, the amount of time between the display of any two consecutive images is random and independent of the amount of time between the display of any two other consecutive images 310. In some embodiments, the amount of time between the display of two consecutive images is randomly chosen from a set of two to ten determined lengths of time.

In some embodiments, the expression images comprise images of human facial expressions. Any image of a human facial expression can be used in the subject systems and methods provided herein. The expression images can depict male and/or female, adult and/or children human facial expression and facial expressions of humans of the same or different ages and ethnicities. In certain embodiments, the expression images of the plurality of expression images are grey scaled. In other embodiments, the expression images of the plurality of expression images are in color. In yet other embodiments, the expression images of the plurality of expression images are a combination of grey scaled and color images. In some embodiments, the expression images are photographs. In some embodiments, the expression images are illustrations. In certain embodiments, the expression images are animated expression images. In some embodiments, expression images are engineered to display a certain intensity of the expression (e.g., level 1 includes expression images with 90% intensity, level 2 includes expression images with 80% intensity, level 3 includes expression images with 70% intensity, level 4 includes expression images with 60% intensity, and level 5 includes expression images with 50% emotion intensity in the images). This contributes to the difficulty of the task across levels. This is purposeful to increase engagement and learning throughout the session.

In some embodiments, the expression images are associated with an expression in a set of expressions. In some embodiments, the set of expressions comprises two, three, four, five, six, seven, eight, nine, or ten different expressions. In some embodiments the set of expressions consists of two, three, four, five, six, seven, eight, nine, ten or more than ten expression selected from the set of expressions {agonized, angry, annoyed, ashamed, bashful, black, bleak, blissful, blithe, bloodthirsty, brooding, cautious, chagrined, choleric, confident, confused, contemptuous, coy, crestfallen, curious, deadpan, dejected, despondent, discouraged, displeased, doleful, dour, downcast, dreamy, delighted, dumbfounded, ecstatic, expressionless, furtive, glazed, gloomy, glowering, glowing, grim, grave, haunted, hot-tempered, frightened, hopeless, hostile, impassive, indignant, inexpressive, intimidating, irate, jeering, languid, leering, mischievous, mocking, pained, pallid, peeved, petulant, pleading, preoccupied, pouting, quizzical, questioning, radiant, resentful, sad, sanguine, sardonic, scornful, scowling, searching, serious, shamefaced, sneering, somber, sour, straight-faced, sullen, sulky, surprised, suspicious, stern, stolid, taunting, tense, threatening, vengeful, wan, wary, wistful, withering, woeful, worried, wrathful, wry, and yearning}. In some embodiments the expression images are facial expressions of a human. However, the present disclosure is not so limiting. In some embodiments are any image that induces amygdala activation (images that are emotionally salient or evocative).

In certain embodiments, the set of expression comprises four different expressions. In particular embodiments, the set of expressions is {happy, worried, angry, and sad} (306). In certain embodiments, the plurality of expression images consists of one image associated with a particular expression in the set of expressions. In other embodiments, the plurality of images consists of two, three, four, five, six seven, eight, nine or ten or more different expression images associated with each expression in the set of expressions.

In some embodiments, the conducting a therapy session 302-326 comprises the step of, responsive to completion of each respective expression image subset within the plurality of expression images, receiving 312 a response from the subject to a query as to whether the first and the last expression image in the respective expression image subset exhibits the same emotion, where each respective expression image subset within the plurality of expression images consists of N sequentially displayed expression images, and where N is a predetermined integer. In certain embodiments of the computing system provided herein, the receiving is performed according to instructions included in a receiving module 128 stored in the subject device memory 120 of a subject device 110.

In some embodiments, N is 1, 2, 3, 4, 5, 6, 7, 8, 9, or 10. In some embodiments, the respective expression image subsets are non-overlapping, meaning that there are no expression images common between respective expression image subsets. In certain embodiments, the respective expression subsets are overlapping. In certain embodiments, each respective expression subset consists of N images and N−1 of these images are found in another expression subset in the plurality of expression subsets.

In particular embodiments, the respective expression image subsets overlap by N−1 expression images 314. As such, consecutive expression image subsets in these embodiments differ by one expression image. For example, for a plurality of images that are sequentially displayed as:

A, B, C, D, E, F, G, H, I, J, K, L, M, where each expression image subset contains N=4 sequentially displayed expression images, the expression image subsets that overlap by N−1 expression images are 1) A, B, C, D; 2) B, C, D, E; 3) C, D, E, F; 4) D, E, F, G, etc. . . .

As such, for expression image subsets that overlap by N−1, the completion of the display of an expression image subset after the completion of the first expression image subset occurs after the display of each image after the first N images.

In certain embodiments, there are ten to twenty respective expression image subsets in the plurality of expression images that are sequentially displayed 316. In other words, there are ten to twenty responses received from the subject in such embodiments. In particular embodiments, there are twenty respective expression image subsets in the plurality of expression images that are sequentially displayed 316.

In some embodiments, the conducting a therapy session 302-326 comprises the step of determining a score 318 for each respective expression image subset within the plurality of expression images based at least in part upon (a) the response to the query for the respective expression image subset, (b) the expression associated with the first expression image in the respective expression image subset, and (c) the expression associated with the last expression image in the respective expression image subset, thereby determining a plurality of scores. In certain embodiments of the computing system provided herein, the determining is performed according to instructions included in a determining module 132 stored in the subject device memory 120 of a subject device 110. In some embodiments, the plurality of scores is determined as the total number of correct responses by the subject to the query as to whether the first and last expression image in a respective expression image subset exhibits the same emotion 320.

In some embodiments, the conducting a therapy session 302-326 comprises the step of resetting (322) the value of N to a new positive integer value based at least in part on the plurality of scores. In certain embodiments of the computing system provided herein, resetting 322 is performed according to instructions included in a resetting module 134 stored in the subject device memory 120 of a subject device 110.

In certain embodiments, the resetting of N is based at least in part on the percentage of correct responses by the subject to the query as compared to the total number of responses 324. In some embodiments, N is reset to N+X if the percentage of correct responses is greater than a set threshold percentage, wherein X is 1, 2, 3, 4, or 5. In certain embodiments, N is reset to N+1 if the percentage of correct responses is greater than 80%-90%. In certain embodiments, N is reset to N+1 if the percentage of correct responses is greater than 80%, 81%, 82%, 83%, 84%, 85%, 86%, 87%, 88%, 89%, or 90%. In some embodiments, N is reset to N−X if the percentage of correct responses is less than a set threshold percentage, wherein X is 1, 2, 3, 4, or 5. In some embodiments, N is reset to N−1 if the percentage of correct responses is less than 55-70%. In some embodiments, N is reset to N−1 if the percentage of correct responses is less than 60%, 61%, 62%, 63%, 64%, 65%, 66%, 67%, 68%, 69%, or 70%. In some embodiments, N is not reset if the percentage of correct responses is within a particular range of percentages. In certain embodiments, N is reset to N+1 if the percentage of correct responses is greater than a first threshold percentage, N is reset to N−1 if the percentage of correct responses is less than a second threshold percentage and N does not reset if the percentage of correct responses is between the first and second threshold percentage 326. In certain embodiments, the first threshold percentage is about 85% and the second threshold percentage is about 65%.

In some embodiments, the therapy session comprises repeating the displaying i) receiving ii), determining iii), and resetting iv) a plurality of times (328). In particular embodiments, the repeating occurs prior to prescribing a treatment regimen (334). In certain embodiments, the repeating is on a recurring basis over the course of a period of time prior to prescribing a treatment regimen. In certain embodiments, the repeating is on a recurring basis over the course of a number of weeks prior to prescribing a treatment regimen.

In some embodiments, the repeating is on a recurring basis over a period of time prior to prescribing a treatment regimen, the subject undergoes the therapy session, and is also intermittently evaluated for one or more symptoms of the psychiatric disorder being treated. In certain embodiments, the computing system described herein includes one or more programs that include instructions for intermittently evaluating the subject for one or more symptoms of the psychiatric disorder being treated. In particular embodiments, the instructions comprise instructions for performing a patient health questionnaire (PHQ) check (e.g., PH-QA, PHQ-2, PHQ-8, PHQ-9, PHQ-15, GAD-2, GAD-7, etc.). See, e.g., Kroenke et al., General Hospital Psychiatry 32: 345-359 (2010), which is hereby incorporated by reference. For instance, in certain embodiments, the subject undergoing the therapy session is also evaluated for cognitive biases and/or neurocognition intermittently. Tests for cognitive biases include, for example, self-referential information processing (SRIP) task, cognitive style questionnaires (CSQ) and ruminative responses scale (RRS). Tests for neurocognition include tests for working memory, for example, tests that test digit-span forward and back, and letter number sequencing. In certain embodiments, the computing system described herein also includes one or more programs that include instruction for intermittently evaluating the subject's cognitive biases and/or neurocognition.

As used herein, a "block" with respect to the therapy session described herein refers to one iteration (instance) of the steps of displaying i) receiving ii), determining iii), and resetting iv). In some embodiments, the therapy session comprises 3 to 200 blocks. In certain embodiments, the therapy session comprises 3 to 15 blocks. In certain embodiments, the therapy session comprises 3 to 15 blocks that occur prior to prescribing a treatment regimen 334.

In some embodiments, the method provided herein comprises the step of prescribing a treatment regimen to the subject based at least in part on the reset value of N (334). In some embodiments, the prescribing comprises communicating the score to a remote server (e.g., a psychiatric disorder treatment server 102) for evaluation by a prescribing clinician 336. In some embodiments, the communicating is performed by the prescribing program 136, located in the subject device memory 120 of the subject device 110 described herein. In certain embodiments, the treatment regimen comprises a frequency of conducting the therapy session and an absolute number of times to conduct the therapy session 338. In certain embodiments the therapy session comprises three or more blocks, sequential blocks are grouped into levels, where each level comprises an equal number of blocks. For example, in certain embodiments, the therapy session comprises performing 15 blocks and 5 levels, where each of the 5 levels consists of 3 blocks. In certain embodiments, the prescribing a treatment regimen is based at least in part on the average of the reset value of N in the last block of every level.

In some embodiments, the treatment regimen comprises a frequency of conducting the therapy session an absolute number of times to conduct the therapy session and the use of a pharmaceutical composition 340, a brain stimulation intervention 342, and/or an empirically supported psychotherapy 344. Without being bound by any particular theory of operation, it is believed that combining different approaches (e.g., medications, brain stimulation interventions and psychotherapies) that target overlapping neural system provides additive effects in the treatment of affective disorders. In certain embodiments, the treatment regimen is characterized by a frequency of conducting the therapy session (e.g., once a week, twice a week, three times a week, daily, every other week), an absolute number of times to conduct the therapy session (e.g., 10 times, 20 times, 30 times), and the use of a pharmaceutical composition 340. In certain embodiments, the treatment regimen is characterized by frequency of conducting the therapy session (e.g., once a week, twice a week, three times a week, daily, every other week), an absolute number of times to conduct the therapy session (e.g., 10 times, 20 times, 30 times), and the use of a brain stimulation intervention 342. In certain embodiments, the treatment regimen is characterized by frequency of conducting the therapy session (e.g., once a week, twice a week, three times a week, daily, every other week), an absolute number of times to conduct the therapy session (e.g., 10 times, 20 times, 30 times), and the use of an empirically supported psychotherapy 344. In other embodiments, the treatment regimen is characterized by frequency of conducting the therapy session (e.g., once a week, twice a week, three times a week, daily, every other week), an absolute number of times to conduct the therapy session (e.g., 10 times, 20 times, 30 times), the use of a pharmaceutical composition 340 and the use of a brain intervention mechanism 342. In other embodiments, the treatment regimen is characterized by frequency of conducting the therapy session (e.g., once a week, twice a week, three times a week, daily, every other week), an absolute number of times to conduct the therapy session (e.g., 10 times, 20 times, 30 times), the use of a pharmaceutical composition 340 and the use of an empirically supported psychotherapy 344. In yet other embodiments, the treatment regimen is characterized by frequency of conducting the therapy session (e.g., once a week, twice a week, three times a week, daily, every other week), an absolute number of times to conduct the therapy session (e.g., 10 times, 20 times, 30 times), the use of a brain intervention mechanism 342 and the use of an empirically supported psychotherapy 344. In yet other embodiments, the treatment regimen is characterized by frequency of conducting the therapy session (e.g., once a week, twice a week, three times a week, daily, every other week), an absolute number of times to conduct the therapy session (e.g., 10 times, 20 times, 30 times), the use of a pharmaceutical composition 340, the use of a brain intervention mechanism 342, and the use of an empirically supported psychotherapy 344.

In certain embodiments, the treatment regimen is characterized by frequency of conducting the therapy session (e.g., once a week, twice a week, three times a week, daily, every other week), an absolute number of times to conduct the therapy session (e.g., 10 times, 20 times, 30 times), and the use of a pharmaceutical composition (340). The pharmaceutical composition prescribed will depend on the psychiatric disorder being treated. Pharmaceutical compositions known for treating an affective disorder include, but are not limited to, selective serotonin reuptake inhibitors (SSRI, e.g., fluoxetine, sertraline, paroxetine, citalopram, escitalopram, dapoxetine, seproxetine, mesembrin, and zimelidine), serotonin norepinephrine reuptake inhibitors (SNRI, e.g., venlafaxine, desvenlafaxine, duloxetine, milnacipran, levomilnacipran, and sibutramine), cognitive enhancers (e.g., adderall, ritalin, dexadrin, modafinil), ketamine and ketamine derivatives, atypical antipsychotics, benzodiazepines, bupropion, amotrigine, lithium, monoamine oxidase inhibitors, tricyclic antidepressants, valproic acid, nefazodone, trazodone, and pramipexole. For suitable dosaging and selection of some such compounds, see U.S. Pat. No. 8,785,500, entitled "Intranasal Administration of Ketamine to Treat Depression," which is hereby incorporated by reference herein in its entirety for such purpose.

In certain embodiments, the psychiatric disorder is MDD and the pharmaceutical composition is an SSRI, an SNRI, a cognitive enhancer, ketamine or a ketamine derivative, an atypical antipsychotic, a benzodiazepine, bupropion, amotrigine, lithium, a monoamine oxidase inhibitor, a tricyclic antidepressant, valproic acid, nefazodone, trazodone, pramipexole or combinations thereof. In certain embodiments, the psychiatric disorder is post traumatic stress disorder (PTSD) and the pharmaceutical composition is an SSRI, an SNRI, a cognitive enhancer, ketamine or a ketamine derivative or combinations thereof. In other embodiments, the psychiatric disorder is general anxiety disorder and the pharmaceutical composition is an SSRI, an SNRI, a cognitive enhancer or combinations thereof.

In some embodiments, the psychiatric disorder is social phobia and the pharmaceutical composition is an SSRI, an SNRI, a cognitive enhancer or combinations thereof. In other embodiments, the psychiatric disorder is obsessive compulsive disorder and the pharmaceutical composition is an SSRI, a cognitive enhancer or combinations thereof. In some embodiments, the psychiatric disorder is borderline personality disorder and the pharmaceutical composition is an SSRI, an SNRI, ketamine or ketamine derivative, a cognitive enhancer or combinations thereof.

In some embodiments, the treatment regimen is characterized by a frequency of conducting the therapy session, an absolute number of times to conduct the therapy session, and the use of a brain stimulation intervention 342. In some embodiments the brain intervention targets the amygdala and dorsolateral prefrontal cortical (DLPFC) brain regions. Without being bound by any particular theory of operation, it is believed that neural circuitry abnormalities within these regions cause the subsequent biased and prolong processing of negative emotional information associated with some affective disorders (e.g., MDD). In some embodiments, the brain target intervention activates the amygdala and DLPFC regions. In some embodiments the brain target intervention is transcranial direct current stimulation, deep brain stimulation and/or transcranial magnetic stimulation (TMS).

In some embodiments, where the therapy session comprises repeating the displaying i) receiving ii), determining iii), and resetting iv) a plurality of times (328) prior to prescribing a treatment regimen, one or more brain target interventions described herein can be administered concurrently during the therapy session or prior to conducting a therapy session. Further, in some embodiments, one or more of the pharmaceutical compositions disclosed herein may be administered prior to conducting the therapy session or after the therapy session, as part of a treatment regimen.

In certain embodiments, the treatment regimen is characterized by frequency of conducting the therapy session (e.g., once a week, twice a week, three times a week, daily, every other week), an absolute number of times to conduct the therapy session (e.g., 10 times, 20 times, 30 times), and the use of an empirically supported psychotherapy 344. In certain embodiments, the empirically supported psychotherapy is a cognitive-behavioral psychotherapy.

In certain embodiments, the computing system described herein includes one or more programs that include instructions for conducting an initial assessment of the subject prior to conducting the therapy in order to select the therapy session from among a plurality of therapy session protocols 302. In certain embodiments, the initial assessment comprises assessing the user subject for one or more symptoms of the affective disorder being treated. In particular embodiments, the instructions comprise instructions for performing a patient health questionnaire check (e.g., PHQ-2, PHQ-9, PHQ-15, GAD-7, etc.). In certain embodiments, the subject is also initially assessed for cognitive biases, neurocognition, and/or emotional function intermittently. In certain embodiments, the computing system described herein also includes one or more programs that include instruction for intermittently evaluating the subject's cognitive biases and/or neurocognition.

In some embodiments, a performance evaluation is provided to the user after the completion of a block, a plurality of blocks or a therapy session. In certain embodiments, one or more programs of the computing system provided herein include instructions for generating a performance evaluation. In some embodiments, the performance evaluation is based on the reset value of N at the completion of a block, a plurality of blocks, or a therapy session. In some embodiments wherein the therapy session is carried out in levels of blocks, the performance evaluation is based on the average of the reset values of N of the last block at every level.

EXAMPLES

Example 1. Cognitive-Emotional Training as an Intervention for Major Depressive Disorder There is an urgent need for more effective treatments for affective disorders, including, for example, major depressive disorder (MDD). As understanding of the cognitive and affective neuroscience underlying psychiatric disorders expands, so do opportunities to develop interventions that capitalize on the capacity for brain plasticity. Cognitive training is one such strategy. A novel cognitive-emotional training exercise designed to enhance cognitive control for emotional information-processing and targeting components of the neural networks that have been implicated in MDD is shown below.

E-1-1. Methods and Materials.

E-1-1-1 Participants.

Twenty-one currently un-medicated MDD participants were recruited through advertisements for depression research studies. Participants between ages 18-55 were diagnosed by trained masters and doctoral-level clinicians using the Structured Clinical Interview for DSM-IV-TR Axis I Disorders (SCID). Participants met criteria for MDD diagnosis and could have other Axis I diagnoses (excluding psychotic disorders, bipolar disorders and substance abuse or dependence within the past six months) if the MDD diagnosis was primary. MDD severity, as measured by the Hamilton Depression Rating Scale (Ham-D)-17 item version, had to be moderate (Ham-D>16), and participants with very severe MDD (Ham-D>27) were excluded and referred for treatment due to safety concerns of participating in an unproven antidepressant study. Participants with a history of treatment non-response (2+ failures of an adequate trial of a standard antidepressant medication) or chronic, non-episodic MDD were excluded from participation, as were participants with visual or motor impairment that would interfere with performance on the computerized exercise. Thirty potential participants were screened for the study; six did not meet inclusion/exclusion criteria and three were eligible but decided not to participate.

The Program for the Protection of Human Subjects at Mount Sinai approved the protocol and study procedures, which were conducted in accordance with the Declaration of Helsinki. After screening, eligible participants were informed about the study procedures and signed informed consent. Participants were informed that the study would evaluate the effects of two different memory training exercises on memory and MDD symptoms. This was not presented as an intervention study, and participants were not informed of the differences between the cognitive-emotional and control training paradigms, thereby maintaining the study blind and minimizing placebo effects. After completing the study, participants were debriefed, including a description of the study blinding involved and the rationale. Participants were reimbursed for each study session completed to compensate for time and travel expenses.

E-1-1-2 Procedure.

The study comprised 11 sessions. In the first, the SCID and Ham-D-17 were administered. A baseline session was then conducted to assess attention and working memory, cognitive processing biases and MDD symptoms. To assess attention span and working memory, a composite score was calculated as the mean scaled score from the Digit-Span Forward (DSF), Digit-Span Backward (DSB) and Letter-Number Sequencing (LNS) subtests of the Wechsler Adult Intelligence Scale-$3^{rd}$ Edition (Wechsler D (1997): Wechsler Adult Intelligence Scale—Third Edition. San Antonio: The Psychological Corporation). Measures of cognitive-processing biases included assessments of rumination (Ruminative Responses Scale (RRS) (Treynor et al., *Cognitive Ther Res* 27: 247-259 (2003)) and negative bias in short-term memory for self-descriptors (Self-Referential Information Processing task; SRIP)(Murray et al., *Memory* 7: 175-196 (1999)). The SRIP involves presenting self-descriptors (positive and negative) and asking the participant to indicate whether the word "sounds like me". Participants are later asked to recall as many of the words as they can remember. The proportion of negative self-descriptors accurately recalled is used as an index of the negative bias in short-term memory in MDD. MDD symptoms were assessed using the Ham-D-17.

Participants were randomly assigned to the cognitive-emotional or control training groups by a research coordinator using a pre-determined sequence for group assignment, generated by an independent biostatistician. Participants completed eight training sessions over 4 weeks (30-45 minutes each, twice per week). Weekly Ham-D assessments were conducted by PhD or MD-level clinicians who were blind to group assignment. Ham-D raters were extensively trained to administer the assessment and demonstrated ICC>0.8 on two separate training interviews. An outcome session was administered within 1 week of completing the training sessions, at which time the baseline assessment was repeated.

E-1-1-3 Cognitive Training Exercises.

The cognitive-emotional training exercise is a combination of emotion identification and working memory tasks: the Emotional Faces Memory Task (EFMT). In this task, participants identify the emotions they observe on a series of pictures of faces presented on a computer screen, and remember the sequence of emotions. Using an N-back working memory training paradigm, for each face observed participants indicate whether the emotion is the same as the emotion N faces back. The N level varies by block depending on performance; N can decrease or increase across blocks. Participants complete 15 blocks per session. Session 1 begins with N=1 and the N for subsequent sessions is determined by performance at the prior session. The task hones in on the participant's ability level while consistently challenging them. In a single, non-progressive session in healthy volunteers, this task simultaneously activated DLPFC and amygdala (Neta et al., *NeuroImage* 56: 1685-1692 (2011)). Progressively challenging n-back working memory tasks have been shown to improve working memory performance (Jaeggi et al, *Proc Natl Acad Sci USA* 105: 6829-6833 (2008)) but a progressively challenging working memory paradigm with emotional stimuli has not yet been reported. The control training (CT) task is an active comparator consisting of an identical cognitive-training paradigm to EFMT except the stimuli were neutral shapes (circle, square, etc.), thereby isolating the simultaneous activation of amygdala and DLPFC to the EFMT group.

E-1-2 Study Design.

The study was designed as a double-blind, randomized, controlled, proof-of-concept trial to determine the effects of a regimen of eight cognitive-emotional training sessions on cognitive-processing biases, working memory and MDD symptoms in MDD participants. As outcome measures, changes in rumination (RRS), short-term memory for positive and negative self-descriptors (SRIP), attention and working memory (DSF, DSB and LNS) and MDD symptoms (Ham-D) were assessed before and after the training regimens.

E-1-3 Data Analytic Strategy.

The effect of EFMT vs. CT training on MDD symptoms was the primary analysis of interest in this proof-of-concept study. A repeated-measures ANOVA of Ham-D change, with group (EFMT v. CT) as the between-factor and time (baseline v. outcome) as the within-factor was planned to investigate the effects on MDD symptoms. Secondary analyses aimed to evaluate changes in cognitive processing biases and working memory. Given the small sample sizes and resulting limited power to detect significant effects, this study planned exploratory analyses of the change within-groups (EFMT or CT) over time, and to estimate effect sizes for the difference in change scores between groups, as the analytic procedure. Effect sizes were of primary interest to begin to describe the possible effects of the cognitive training intervention, and t-tests were conducted within-groups although the power to detect significant p-values ($\alpha<0.05$) was limited. Effect sizes were interpreted as per Cohen 1988 (Cohen J: Statistical Power Analysis for the Behavioral Sciences, 2nd ed. Hillsdale, N.J.: Lawrence Earlbaum Associates (1998)): "small"=$0.2<d<0.3$; "medium"=$d=0.5$; "large"=$d<0.8$. Between-groups analyses of the cognitive variables were not planned due to limited power and the exploratory nature of the analyses.

E-1-4 Results.

Table 1 provides the demographic and clinical characteristics of the study sample. Eleven participants were assigned to EFMT and ten to CT. All twenty-one participants completed all 8 training sessions over 4 weeks with no attrition. Performance on the task (mean N-level achieved at each session) improved over time in both groups. At week four the EFMT group achieved a mean N-level of 5.5 and the CT group 5.6.

TABLE 1

Demographic and Clinical Characteristics of the Study Sample

| | EFMT | CT |
|---|---|---|
| Number of patients | 11 | 10 |
| Age (years) | 36.33 (8.5) | 39.5 (8.19) |
| Gender | 6 Female, 5 Male | 5 Female, 5 Male |
| Ethnicity | 5 African-American<br>4 Caucasian<br>2 Asian | 5 African-American<br>5 Caucasian |
| Baseline Depression Severity (Ham-D-17) | 21.55 (2.97) | 19.80 (2.79) |
| Duration of current MDD episode (months) | 20.9 (6.4) | 19.1 (7.5) |
| Number of previous MDD episodes | 1.9 (.65) | 1.84 (.49) |
| Axis I Comorbidities (current) | 27% Social Phobia<br>18% Generalized Anxiety<br>18% PTSD | 20% Social Phobia<br>20% Generalized Anxiety<br>10% PTSD |

Note:
Standard deviation in parenthesis.

Figure 4A:
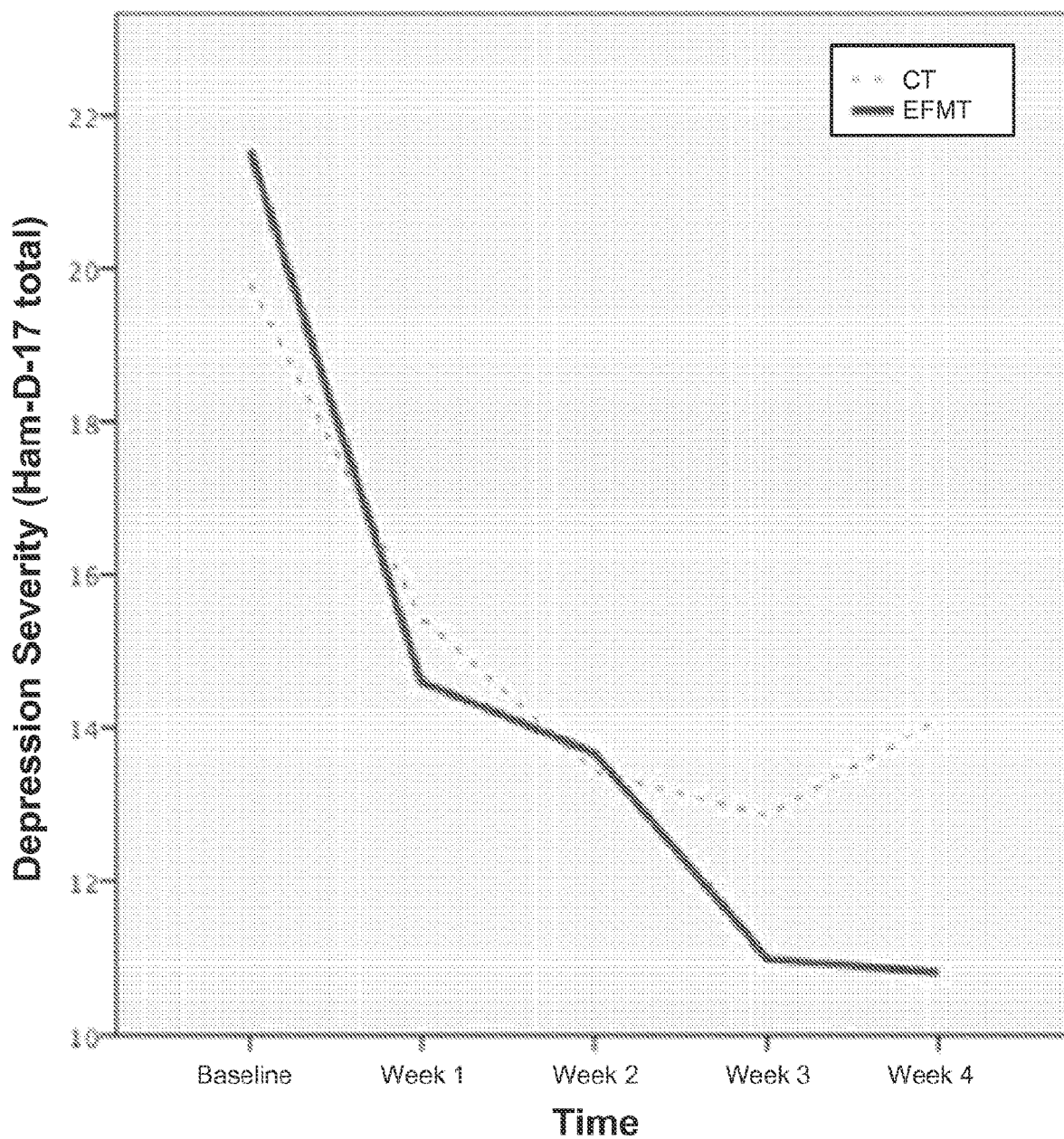
FIG. 4A is a graph showing the change in depression severity over time between a group having MDD undergoing an EFMT therapy session and a CT control group. As shown in the graph, the EFMT group demonstrated a significant reduction (from 21.55 to 10.91; p<0.001, d=2.67) that was greater than the CT group (from 19.80 to 14.10; p=0.01, d=1.08). The difference between groups in change in MDD symptoms over time (EFMT=−10.64; CT=−5.7) was large: d=0.82.

FIG. 4A depicts a reduction in mean Ham-D scores between baseline and outcome in the EFMT group from 21.55 to 10.91 that was significantly larger than the reduction in the CT group from 19.80 to 14.10 (Group [EFMT v. CT]×Time [baseline v. outcome] ANOVA: $F(1, 19)=5.605$, $p=0.029$). At week 4, the difference in Ham-D scores between groups approached significance, $t(19)=1.91$, $p=0.07$. Both groups showed main effects of time in Ham-D reduction (EFMT: $t(10)=8.86$, $p<0.001$; CT: $t(9)=3.27$, $p=0.01$). The effect size for the difference between groups in change in MDD symptoms over time (ΔHam-D: EFMT=−10.64; CT=−5.7) was large: $d=0.82$. Six of the 11 EFMT participants, and one of the ten CT participants, achieved ≥50% reduction in Ham-D score between baseline and outcome, which is the standard for defining a "responder" in clinical MDD trials.

Figure 4B:
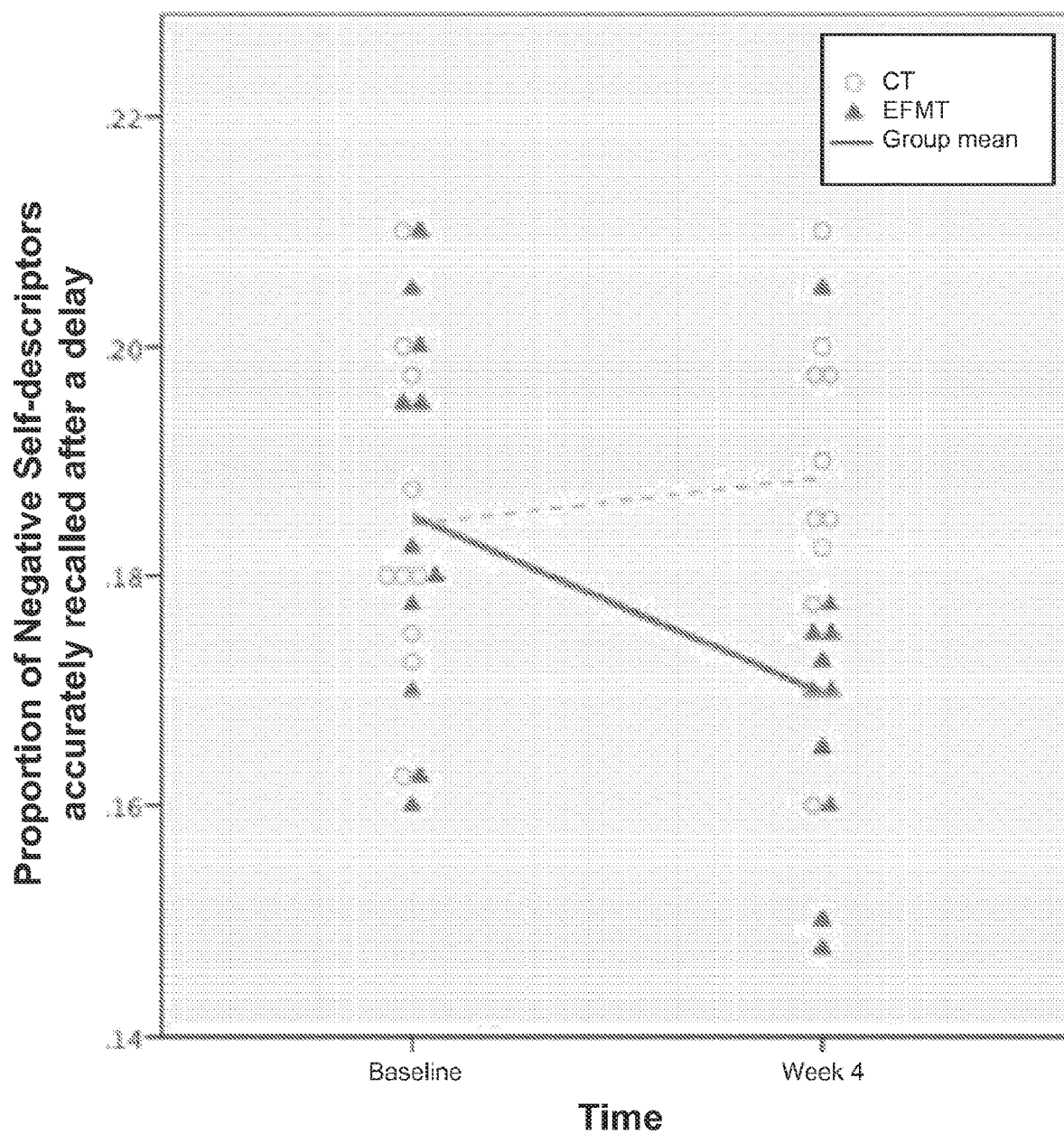
FIG. 4B is a graph showing the change in negative affective bias in short-term memory over time between a group having MDD undergoing an EFMT therapy session and a CT control group. As shown in the graph, EFMT participants demonstrated a significant reduction in short-term memory for negative self-referential information (proportion of negative self-descriptors accurately recalled after a delay) from 0.1852 to 0.1697 (p=0.037, d=−0.79), whereas the CT group showed a small and non-significant increase from 0.1845 to 0.1885 (p=0.535, d=0.27). The between-groups difference in change was medium-sized: d=0.60.

The EFMT group demonstrated a medium-size but non-significant reduction in rumination (RRS) scores from 28.45 to 25.45, $t(10)=1.54$, $p=0.14$, $dΔ=−0.66$. The CT group demonstrated a small, non-significant increase from 28.8 to 30.6, $t(9)=0.88$, $p=0.39$, $dΔ=0.39$. The effect size for the difference between groups in rumination change over time was medium-sized: $d=0.64$. On the Self-Referential Information Processing (SRIP) task, the EFMT group showed a significant reduction in short-term memory for negative self-referential information (proportion of negative self-descriptors accurately recalled after a delay) from 0.1852 to 0.1697, $t(10)=2.23$, $p=0.037$, $dΔ=−0.79$. The CT group showed a small, non-significant increase from 0.1845 to 0.1885, $t(9)=0.63$, $p=0.535$, $dΔ=0.27$ (see FIG. 4B). The effect size for the difference in change scores between groups was medium-sized: $d=0.60$.

Both groups demonstrated similar, small improvements in attention span and working memory after training (DSF, DSB and LNS composite score). The EFMT group demonstrated an increase from 10.3 to 11.36 ($t(10)=1.855$, $p=0.09$, $dΔ=0.31$), the CT group demonstrated an increase from 10.8 to 11.25 ($t(9)=1.01$, $p=0.34$, $dΔ=0.20$), and the composite scores were not significantly different between groups at baseline or at week 4.

E-1-5 Conclusion.

The differential effects of EFMT versus CT in this study indicate that cognitive-emotional training can be an intervention strategy for MDD, targeting impaired cognitive control for emotional information processing and the underlying neural network functioning abnormalities. These interventions can be feasible and relatively low-cost, eventually disseminated to a participant's home via computer. Such interventions can serve as an augmentation strategy for traditional interventions such as medications or cognitive-behavioral therapy. Additionally, these types of interventions may be accessible for populations that cannot make use of traditional interventions (pregnant females or medically ill individuals for whom antidepressant medications are not indicated, for example).

Example 2. Clinical Trial

The objective of this trial is to investigate the effectiveness of the disclosed computerized training paradigm to modify the negative bias in working memory and whether improvement in this domain transfers to other domains of cognitive processing that are also impaired in depression (facial emotion recognition, self-referential information processing and attribution style).

As such, one specific aim of this trial is to measure the effectiveness of the Emotional Faces Memory Task in reducing depressive symptoms in major depressive disorder (MDD) participants compared to the placebo control task (PCT). It is believed that MDD participants undergoing six weeks of EFMT training will demonstrate greater improvement of depressive symptoms than MDD participants undergoing the PCT.

Another specific aim of this trial is to measure the effects of EFMT on negative affective biases in information-processing. It is believed that EFMT training, compared to PCT, will result in reduced negative affective bias in information processing.

Another specific aim of this trial is to measure the neurocognitive effects of EMFT training. It is believed that both EFMT and PCT training groups will show improvement across neurocognitive domains.

Major depressive disorder (MDD) is a common, severe, chronic and often life-threatening illness that affects approximately 17% of the general population. The impairment in physical and social functioning resulting from MDD can be as severe as other chronic medical illnesses. Despite important advances in the treatment of depression, many patients with this illness remain inadequately treated, often due to treatment noncompliance. It is estimated that only 60 to 70% of patients treated with an antidepressant respond to the initial trial of pharmacotherapy. As MDD continues to pose a significant public health problem, with high rates of morbidity and mortality, well-tolerated new interventions are necessary.

Research has consistently documented that depressed individuals demonstrate a negative affective bias such that they tend to bias perception and processing towards negative information as compared to positive or neutral information. This negative affective bias has been documented in several domains of perception and processing including working memory, emotional processing, self-referential information processing and attributional style. Importantly, the presence of a negative affective bias across each of these domains of processing in depression may be due to shared underlying neural circuitry. Indeed, the brain regions involved in each of these domains of perception and processing are all part of larger networks that have been implicated in normal emotion perception as well as the pathophysiology of depression. Recent research has been aimed at modifying various cognitive biases in depression and anxiety disorders through cognitive training, with promising initial results.

E-2-1 Study Design.

E-2-2 Recruitment Methods.

Subjects are recruited through advertisements in local newspapers and websites such as craigslist and clinical connections. Participants are also recruited through the ongoing, IRB approved, MAP recruitment and screening protocol.

E-2-2-1 Inclusion and Exclusion Criteria.

Inclusion criteria are (i) primary, current axis I diagnosis of major depressive disorder according to DSM-IV criteria and a Ham-D-17 score between 16-27, (ii) age between 18 and 55, and (iii) an ability to give informed consent. As such, patients with a primary diagnosis of major depressive disorder are admitted. Moreover, some patients also have comorbid (secondary) affective disorder diagnoses such as posttraumatic stress disorder, social phobia, generalized anxiety disorder, specific phobias, and borderline personality disorder and the disclosed trial and the disclosed systems and methods is expected to improve symptoms (reduction of at least 50% in depression symptoms) of such patients as well.

Exclusion criteria are any of (i) a history of drug or alcohol abuse or dependence (DSM-IV criteria) within 6 months, (ii) visual impairment that would affect the ability to observe the computerized presentation of faces or other images that induce induce amygdala activation, (iii) motor impairment that would affect the ability to provide a response by quickly pressing a button, (iv) lifetime history of bipolar spectrum disorders or schizophrenia spectrum disorders, (v) primary, current Axis I diagnosis other than major depressive disorder, (vi) primary, current Axis II personality disorder, (vii) currently attending a cognitive-behavioral psychotherapy regimen, (viii) acute suicidal or homicidal risk (evidenced by suicidal or homicidal attempt within 6 months of screening), and (ix) pregnancy.

Enrolled participants can be currently taking medication but are stabilized on their medication regimens before enrolling in the study (i.e., no medication has been started within 8 weeks, stopped within 6 weeks or titrated up or down within 4 weeks of study entry). Accordingly, if a patient's medication status must change during the course of the study, are discontinued from the study. No medications are discontinued for the purpose of enrollment into the study.

Subjects exhibit no or only moderate alcohol use. Subjects with current excessive use of alcohol (>8 ounces/day for men and >6 ounces/day for women) are ineligible for participation, as such drug use could confound the results. The target recruitment for this study is eighty people.

E-2-2 Study Timelines.

E-2-2-1 Individual Subjects' Participation.

All participants require baseline behavioral assessment measures. They are then randomly assigned to either a training group or control group, and required to make 18 three-times-weekly appointments over 6 weeks. The estimated duration of an individual subject's participation is that is last 10 weeks depending on scheduling flexibility for diagnostic, baseline and post measures. The approximate recruitment duration is five years.

E-2-2-2 Study Endpoints.

This study ends once target recruitment goals have been met.

E-2-3 Procedures Involved.

A double-blind randomized design is used in which depressed subjects are assigned to undergo one of two procedures: the Emotional Faces Memory Task (EFMT) training paradigm or a placebo control task (PCT) which is a computer task designed to match the number of sessions attended and exposure to computerized stimuli. Subjects initially undergo a screening and diagnostic evaluation to determine eligibility for participation. Upon meeting inclusion criteria, participants are assigned to either the training group or the control group, based on a predetermined randomization algorithm that includes medication status as a factor. An initial session to obtain baseline levels of depression symptoms (BDI-II), rumination (RRS), neuropsychological functioning (DS and LNS), verbal memory (HVLT), facial emotion recognition ability (EFRT), cognitive/affective processing biases (eStroop and Affective Go/No-Go (AGNG)), and outcome measures (CSQ, SRIP, and LOT-R) is then conducted. All participants attend 18 sessions during which they either receive the training paradigm or the placebo control task. After the 18 sessions, the baseline assessments are repeated.

E-2-4 Screening Interview (Approximately 1 Hour).

Subjects referred to the study or responding to advertisements for the study are educated about the protocol. Subjects interested in participating sign a consent form in order to proceed with a screening and diagnostic interview. This interview includes collecting demographic information and a psychosocial battery including a diagnostic interview (SCID) and Hamilton Rating Scale for Depression (Ham-D-17) to confirm MDD diagnosis and to rule out exclusion criteria.

Individuals who are screened for the study and are found to have a previously undiagnosed psychiatric disorder or medical condition are made aware of the diagnosis/condition and are provided with referrals (either to their current primary care physician or to another appropriate referral) for treatment or further consultation if they so desire.

E-2-5 Baseline Assessment (Approximately 2.5 Hours).

Participants attend a baseline assessment session at which time they are administered a self-report assessment of depression symptoms (the Beck Depression Inventory-II (BDI-II), rumination (RRS), and an assessment of neuropsychological functioning (Digit Span and Letter-Number Sequencing) and verbal memory (HVLT). At this session, participants are administered secondary measures, to attain a baseline. These include the Emotion Faces Recognition Task (EFRT), emotional Stroop (eStroop), Affective Go/No-go (AGNG), Cognitive Style Questionnaire (CSQ), the Self-Referential Information Processing (SRIP) task, and an Optimism questionnaire (LOT-R). At this session, to assess the acceptability of cognitive training as a potential intervention strategy for depression, participants will be asked to rate the acceptability on a single Likert-scale item.

E-2-6 Training Sessions or Control Group Sessions (35 Minutes Each).

The training condition is three-times-weekly for 6 weeks (18 sessions total). Subjects in the training condition complete the EFMT task for the purposes of increasing their ability to accurately identify and remember facial emotions. For the control condition, the control group attend three-times-weekly sessions for 6 weeks, at which they complete the Placebo Control Task (PCT), and an adaptive n-back working memory assessment using shapes as the stimuli. This is to control various confounding factors that could potentially impact the outcome variables, such as improvement in working memory due to training, the number of sessions attended, interactions with study staff and placebo effects due to expectations for improvement based on attending a cognitive training.

E-2-7 Mid-Study Assessment (Week 3; Approximately 45 Minutes).

At the mid-study assessment session, to take place at the end of the participants' third week of training, participants complete the RRS, eStroop, EFRT and AGNG to monitor changes in cognitive and affective processing that might precede changes in mood symptoms.

E-2-8 Outcome Assessment (Approximately 2.5 Hours).

At the outcome assessment session, participants complete the BDI-II, RRS, DS, LNS, HVLT, EFRT, eStroop, AGNG, CSQ, SRIP, and LOT-R. At this session, participants also complete a questionnaire to rate 1) the acceptability of cognitive training for depression as a possible intervention strategy; 2) the perceived helpfulness of the cognitive training regimen they participated in. Ratings are provided on two likert-scale items, respectively.

E-2-9 Follow-Up Assessments (Approximately 0.5 Hours Each).

Study completers (participants who complete at least 15 training sessions and the baseline and outcome sessions) are interviewed at 2-weeks, 4-weeks, 6-weeks, 8-weeks, 16-weeks and 24-weeks after the Outcome Assessment to collect pilot data on the course of MDD symptoms after the EFMT and PCT regimens. Follow-up assessments will involve the Ham-D interview administered by trained study clinicians.

E-2-10 Suicidality Assessments.

Upon study enrollment, participants discuss with a study investigator the plan for monitoring and handling emergent suicidality during study participation. Participants are provided with the PI's direct contact number (including cell phone number provided on the consent form) and encouraged to call if suicidal thinking emerges or worsens. The participant also identifies the emergency room closest to their home, and is instructed to call 911 or 1-800-LIFE-NET or go to the nearest emergency room in the event that they feel they are in danger of harming themselves and they are unable to contact the PI (or if they feel it is an emergency that cannot wait for contacting the PI).

The baseline assessment and the outcome assessment sessions also include an assessment of suicidal ideation. Moreover, every week throughout the study patients meet briefly with a study clinician (a licensed clinical professional; MD Psychiatrist or PhD Clinical Psychologist) to ask about their mood and any suicidal ideation they have experienced since the last session, using a standardized and validated assessment of suicidality (the Columbia Suicide Severity Rating Scale, C-SSRS) and clinician rated improvement/worsening scale (CGI) for study data collection purposes.

In addition to the weekly depression and suicidality symptom assessment conducted by the study investigators (including standardized rating scales: Columbia Suicide Severity Rating Scale (CSSRS) and Hamilton Depression Rating Scale (Ham-D)), all patients are interviewed weekly by a NON-STUDY (not a study investigator, mentor or collaborator, as per the K23 application), licensed clinician from within the Mood and Anxiety Disorders Program (MAP) at Mount Sinai. Licensed clinicians at MAP have extensive experience assessing and monitoring serious mood and anxiety disorder symptoms and suicidality. These interviews include an assessment of depression symptoms and the occurrence of passive or active suicidal ideation/intent/plan/actions. Significant worsening of symptoms, or increased suicidal ideation, can be a common occurrence in depressed patients but still needs to be taken very seriously. In the event that a patient exhibits significant suicidal ideation, and in the judgment of the interviewer the patient is at risk of harming themselves, then: (i) the patient is escorted to a hospital emergency room for assessment for inpatient hospitalization, and (ii) the patient is withdrawn from the study to obtain necessary treatment. If the patient is not hospitalized, and a treatment plan is not established through the emergency room, then (a) the patient is provided outpatient treatment for three months free of charge. This free follow-up period is offered to all subjects enrolled in MAP studies and can include: evaluation and ongoing treatment with a psychiatrist, including provision of a prescription that can be filled at the patient's local pharmacy; psychotherapy with a psychologist or social worker; or both pharmacotherapy and psychotherapy if warranted. The free follow-up period is also be used by clinicians to advise the patient on finding long-term care in his/her local community, according to their insurance/ability to pay. Clinicians suggest options for long-term treatment and make appropriate referrals. If the patient is already under the care of a mental health treatment provider, and if the patient prefers not to pursue three months of free treatment through MAP, they will be referred back to their treatment provider after consultation with the provider regarding the reasons for study discontinuation and the investigators' concerns about the patient's safety. All study patients sign a waiver at study enrollment that provides the contact information for current treatment providers and grants study investigators the right to contact current treatment providers in the case of emergency or risk of harm.

E-2-11 Data Analytic Strategy.

Aim 1: Measure the effectiveness of EFMT in reducing depressive symptoms in MDD participants compared to PCT. Hypothesis 1: MDD participants undergoing six weeks of EFMT training will demonstrate greater improvement of depressive symptoms than MDD participants undergoing the PCT. Analytic Strategy: intent-to-treat analyses is conducted, including all participants that complete at least 1 week of training. The primary analysis for this proof-of-concept study is based on a Bayesian approach with emphasis on estimating the posterior probability distribution of the mean between-group difference in Ham-D change from baseline to final assessment. This flexible approach allows estimation of the probability that EFMT is superior to PCT in reducing Ham-D scores by any amount (e.g., more than 0, more than 2, etc.), in addition to providing a test of the corresponding frequentist null hypothesis of no difference. This approach assumes a non-informative diffuse normal prior probability distribution for the difference in Ham-D scores between groups, reflecting a null hypothesis of no difference (e.g., a N(0,25) prior). This prior distribution is updated by incorporating observed results, and the resulting posterior distribution used to compute the probability that EFMT is superior to PCT by any specified amount. In addition to the Bayesian analysis, a more traditional intent-to-treat analysis of covariance (ANCOVA) is conducted to determine the adjusted (for baseline and number of training sessions) difference in Ham-D scores between EFMT and PCT groups. In this ANCOVA the factor is group (EFMT or PCT), final Ham-D score is the dependent variable, baseline Ham-D score and the number of training sessions completed are covariates.

E-2-12 Aim 2.

Measure the effects of EFMT on negative affective biases in information-processing. Hypothesis 2: EFMT training will result in reduced negative affective bias in information processing. Analytic Strategy: ANCOVAs are conducted to evaluate changes in cognitive/affective processing assessments between EFMT and PCT groups. In separate ANCOVA analyses for each measure, the factor will be group (EFMT or PCT) and final score (RRS, eStroop, AGNG, EFRT, LOT-R, SRIP or CSQ) is the dependent variable, with baseline score and number of training sessions completed as covariates.

E-2-13 Aim 3.

Measure the neurocognitive effects of EMFT training. Hypothesis 3: EFMT and PCT groups will show similar improvement in neurocognition. Analytic Strategy: ANCOVAs is conducted for the effect of training on (1) attention and memory span (DSF), (2) working memory (DSB and LNS composite score) and (3) verbal memory (HVLT). Participants who fail to reach a mean performance level of 2.5 on the cognitive training task for at least one week of training (during any week of the study) are excluded from the final data analysis.

E-2-14 Intermediate Results.

Table 2 provides intermediate results for a 23 patient group in which there were 12 patients in group A and 11 in group B. The goal of this blinded study data is to show that participants in one of the study groups are meeting clinical response criteria (reduction of at least 50% in depression symptoms) much more frequently than in the other group. This indicates that the intervention provided for this group is more effective in reducing MDD symptoms. It is expected that, when the data are unblinded, that this group is the active cognitive-emotional training group. To date, there have been no adverse side effects or other adverse events that have occurred as a result of the clinical trial procedures. Numerous patients have shown significant improvement as a result of their participation in the study, presumably as a result of the cognitive-emotional training intervention, leading to our expectation that the intervention will be found to be effective when the final data are analyzed. In Table 2, the "Baseline" and "Outcome" numbers are the total score on the depression rating scale used in the study (the Hamilton depression rating scale 17-item version (HAM-D-17)). The two values for each patient ("Baseline" and "Outcome") represent the baseline (study beginning) and outcome (study endpoint); the change score is provided as outcome minus baseline; and percent change is change score divided by baseline score (multiplied by 100).

TABLE 2

|  | Baseline | Outcome | Change | % Change |
| --- | --- | --- | --- | --- |
| Group A | | | | |
| 1 | 20 | 12 | −8 | −40 |
| 2 | 18 | 14 | −4 | −22.22 |
| 3 | 18 | 18 | 0 | 0 |
| 4 | 22 | 18 | −4 | −18.18 |
| 5 | 17 | 16 | −1 | −5.88 |
| 6 | 17 | 17 | 0 | 0 |
| 7 | 23 | 25 | 2 | 8.7 |
| 8 | 22 | 25 | 3 | 13.64 |
| 9 | 22 | 19 | −3 | −13.64 |
| 10 | 16 | 10 | −6 | −37.5 |
| 11 | 16 | 7 | −9 | −56.25 |
| 12 | 19 | 15 | −4 | −21.05 |
| A_mean | 19.16667 | 16.33333 | −2.83333 | −16.0317 |
| Group B | | | | |
| 1 | 18 | 5 | −13 | −72.22 |
| 2 | 17 | 4 | −13 | −76.47 |
| 3 | 20 | 10 | −10 | −50 |
| 4 | 19 | 10 | −9 | −47.37 |
| 5 | 16 | 13 | −3 | −18.75 |
| 6 | 21 | 10 | −11 | −52.38 |
| 7 | 19 | 12 | −7 | −36.84 |
| 8 | 26 | 19 | −7 | −26.92 |
| 9 | 21 | 17 | −4 | −19.05 |
| 10 | 17 | 8 | −9 | −52.94 |
| 11 | 16 | 11 | −5 | −31.25 |
| B_mean | 19.09091 | 10.81818 | −8.27273 | −44.0173 |

One of 12 patients in group A "responded" (had at least 50% reduction in symptoms); whereas 5 of 11 in group B responded. Although formal statistical analyses has not been done at this time (not until the data is unblinded for the interim analysis) the data indicates that there is a statistically significant difference between the groups.

The terminology used in the description of the invention herein is for the purpose of describing particular implementations only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

All references cited herein are incorporated herein by reference in their entirety and for all purposes to the same extent as if each individual publication or patent or patent application was specifically and individually indicated to be incorporated by reference in its entirety for all purposes.

The foregoing description, for purpose of explanation, has been described with reference to specific implementations. However, the illustrative discussions above are not intended to be exhaustive or to limit the invention to the precise forms disclosed. Many modifications and variations are possible in view of the above teachings. The implementations described herein were chosen and described in order to best explain the principles of the invention and its practical applications, to thereby enable others skilled in the art to best utilize the invention and various implementations with various modifications as are suited to the particular use contemplated.

What is claimed is:

1. A computing system, comprising:
one or more processors;
memory; and
one or more programs, wherein the one or more programs are stored in the memory and are configured to be executed by the one or more processors to treat a subject in need of treatment of a psychiatric disorder, the one or more programs including instructions for:
conducting a therapy session, the therapy session comprising:
i) sequentially displaying each respective expression image in a plurality of expression images, the plurality of expression images comprising a plurality of subsets of expression images, wherein each expression image in the plurality of expression images is (a) independently associated with a respective expression in a set of expressions, (b) engineered to display or exhibits a predetermined intensity of the respective expression on an intensity scale that ranges from a first intensity level to a second intensity level of the respective expression and (c) configured to induce human amygdala activation,
ii) responsive to completion of each respective expression image subset within the plurality of expression images, receiving a response from the subject to a query as to whether the first and the last expression image in the respective expression image subset exhibits the same emotion, and wherein each respective expression image subset within the plurality of expression images consists of N expression images, wherein N is a predetermined integer,
iii) determining a score for each respective expression image subset within the plurality of expression images based at least in part upon the response to the query for the respective expression image subset, and
iv) resetting the value of N to a new positive integer value based at least in part on the plurality of scores.

2. The computing system of claim 1, wherein the i) sequentially displaying, ii) receiving, iii) determining, and iv) resetting are repeated a plurality of times in the therapy session.

3. The computing system of claim 1 wherein the predetermined intensity of the respective expression on the intensity scale of respective images of a first subset of expression images in the plurality of expression images is less than the predetermined intensity of the respective expression on the intensity scale of respective images in the plurality of expression images of a second subset of expression images in the therapy session, wherein the second subset is displayed after the first subset.

4. The computing system of claim 1, wherein the set of expressions comprises happy, worried, angry and sad.

5. The computing system of claim 1, further comprising prescribing a treatment regimen to the subject for the psychiatric disorder and wherein the treatment regimen comprises a frequency of conducting the therapy session and an absolute number of times to conduct the therapy session.

6. The computing system of claim 1, further comprising prescribing a treatment regimen to the subject for the psychiatric disorder and wherein the treatment regimen comprises the use of a pharmaceutical composition.

7. The computing system of claim 6, wherein the psychiatric disorder is MDD and the pharmaceutical composition is a selective serotonin reuptake inhibitor (SSRI), a serotonin norepinephrine reuptake inhibitor (SNRT), a cognitive enhancer, ketamine or ketamine derivative, an atypical antipsychotic, a benzodiazepine, bupropion, amotrigine, lithium, a monoamine oxidase inhibitor, a tricyclic antidepressant, valproic acid, nefazodone, trazodone, pramipexole or combinations thereof; or
wherein the psychiatric disorder is post traumatic stress disorder (PTSD) and the pharmaceutical composition is an SSRI, an SNRT, a cognitive enhancer, ketamine or ketamine derivative, or combinations thereof; or
wherein the psychiatric disorder is general anxiety disorder and the pharmaceutical composition is an SSRI, an SNRT, a cognitive enhancer or combinations thereof; or
wherein the psychiatric disorder is social phobia and the pharmaceutical composition is an SSRI, an SNRI, a cognitive enhancer or combinations thereof; or
wherein the psychiatric disorder is obsessive compulsive disorder and the pharmaceutical composition is an SSRI, a cognitive enhancer or combinations thereof; or
wherein the psychiatric disorder is borderline personality disorder and the pharmaceutical composition is an SSRI, an SNRI, ketamine or ketamine derivative, a cognitive enhancer or combinations thereof.

8. The computing system of claim 1, wherein the psychiatric disorder is an affective disorder (AD).

9. The computing system of claim 8, wherein the AD is major depressive disorder (MDD), post traumatic stress disorder (PTSD), general anxiety disorder, social phobia, obsessive compulsive disorder, treatment resistant depression, or borderline personality disorder.

10. The computing system of claim 1, further comprising prescribing a treatment regimen to the subject for the psychiatric disorder and wherein the treatment regimen comprises a frequency of conducting the therapy session, an absolute number of times to conduct the therapy session, and the use of a brain stimulation intervention.

11. The computing system of claim 1, wherein sequentially displaying each respective expression image in a plurality of expression images includes sequentially displaying each respective expression image in a plurality of expression images for a predetermined amount of time for a predetermined amount of time and wherein the predetermined amount of time is less than 10 seconds.

12. The computing system of claim 1, wherein the predetermined amount of time is between 0.2 seconds and 10 seconds.

13. The computing system of claim 1, further comprising prescribing a treatment regimen to the subject for the psychiatric disorder and wherein the prescribing comprises communicating the score to a remote server for evaluation by a prescribing clinician.

14. The computing system of claim 1, wherein the sequentially displaying comprises retrieving the first subset of the plurality of expression images from a database that stores the plurality of expression images, wherein the database stores, for each respective expression image in the plurality of expression images, the emotion associated with the expression image.

15. The computing system of claim 1, wherein the respective expression image subsets are overlapping, and wherein each subset overlaps by N−1 images with another respective image subset.

16. The computing system of claim 1, wherein the plurality of scores is determined as the total number of correct responses from the subject to the query as to whether the first and last expression in the respective expression image subset is the same.

17. The computing system of claim 16, wherein the resetting of N is based at least in part on the percentage of correct responses from the subject to the query as compared to the total number of response.

18. The computing system of claim 17, wherein
N is reset to N+1 when the percentage of correct responses is greater than a first threshold percentage,
N is reset to N−1 when the percentage of correct responses is less than a second threshold percentage, and
N does not reset when the percentage of correct responses is between the first and second threshold percentage.

19. The computing system of claim 1, wherein the one or more programs include instructions for i) conducting an initial assessment of the subject prior to the conducting the therapy to select the therapy session from among a plurality of therapy session treatment protocols; ii) conducting an assessment of the cognitive function or emotional function of the subject after conducting the therapy session, wherein the assessment is used as the basis, at least in part, for the prescribing a treatment regimen to the subject; or iii) providing the subject with a performance evaluation based at least in part on the plurality of scores of a plurality of therapy sessions.

20. The computing system of claim 19, wherein the one or more programs include instructions for providing the subject with a performance evaluation based at least in part on the plurality of scores.

21. The computing system of claim 1, wherein at least one expression image in the plurality of expression images is not a facial expression.

22. The computing system of claim 1, wherein at least one expression image in the plurality of expression images is a facial expression.

23. The computing system of claim 1, wherein the predetermined intensity of the respective expression on the intensity scale of respective displayed expression images increases from the first intensity level to the second intensity level across the therapy session, wherein the first intensity level is less than the second intensity level.

24. A non-transitory computer readable storage medium storing one or more programs configured for execution by a computing device having one or more processors and memory, the one or more programs comprising instructions for:
conducting a session comprising:
i) sequentially displaying each respective expression image in a plurality of expression images, the plurality of expression images comprising a plurality of subsets of expression images, wherein each expression image in the plurality of expression images is (i) independently associated with a respective expression in a set of expressions, (ii) engineered to display or exhibit a predetermined intensity of the respective expression on an intensity scale that ranges from a first intensity level to a second intensity level of the respective expression and (c) configured to induce human amygdala activation,
ii) responsive to completion of each respective expression image subset within the plurality of expression images, receiving a response from a subject to a query as to whether the first and the last expression image in the respective expression image subset exhibits the same emotion, and wherein each respective expression image subset within the plurality of expression images consists of N expression images, wherein N is a predetermined integer,
iii) determining a score for each respective expression image subset within the plurality of expression images based at least in part upon the response to the query for the respective expression image subset, and
iv) resetting the value of N to a new positive integer value based at least in part on the plurality of scores.

25. A method comprising:
conducting a session comprising
sequentially displaying each respective expression image in a plurality of expression images, the plurality of expression images comprising a plurality of subsets of expression images, wherein each expression image in the plurality of expression images is (i) independently associated with a respective expression in a set of expressions, (ii) engineered to display or exhibits a predetermined intensity of the respective expression on an intensity scale that ranges from a first intensity level to a second intensity level of the respective expression and (iii) configured to induce human amygdala activation,
responsive to completion of each respective expression image subset within the plurality of expression images, receiving a response from a subject to a query as to whether the first and the last expression image in the respective expression image subset exhibits the same emotion, and wherein each respective expression image subset within the plurality of expression images consists of N expression images, wherein N is a predetermined integer,
determining a score for each respective expression image subset within the plurality of expression images based at least in part upon the response to the query for the respective expression image subset, and
resetting the value of N to a new positive integer value based at least in part on the plurality of scores.

26. The method of claim 25, wherein the i) sequentially displaying, ii) receiving, iii) determining, and iv) resetting are repeated a plurality of times in the session.

27. The method of claim 25, wherein the predetermined intensity of the respective expression on the intensity scale of respective images of a first subset of expression images in the plurality of expression images is less than the predetermined intensity of the respective expression on the intensity scale of respective images in the plurality of expression images of a second subset of expression images in the session, wherein the second subset is displayed after the first subset.

28. The method of claim 25, wherein the set of expressions comprises happy, worried, angry and sad.

29. The method of claim 25, further comprising prescribing a treatment regimen to the subject for a psychiatric disorder and wherein the treatment regimen comprises a frequency of conducting the session and an absolute number of times to conduct the session.

30. The method of claim 25, further comprising prescribing a treatment regimen to the subject for a psychiatric disorder and wherein the treatment regimen comprises the use of a pharmaceutical composition.

31. The method of claim 30, wherein the psychiatric disorder is an affective disorder (AD).

32. The method of claim 31, wherein the AD is major depressive disorder (MDD), post traumatic stress disorder (PTSD), general anxiety disorder, social phobia, obsessive compulsive disorder, treatment resistant depression, or borderline personality disorder.

33. The method of claim 32, wherein the psychiatric disorder is MDD and the pharmaceutical composition is a selective serotonin reuptake inhibitor (SSRI), a serotonin norepinephrine reuptake inhibitor (SNRT), a cognitive enhancer, ketamine or ketamine derivative, an atypical antipsychotic, a benzodiazepine, bupropion, amotrigine, lithium, a monoamine oxidase inhibitor, a tricyclic antidepressant, valproic acid, nefazodone, trazodone, pramipexole or combinations thereof; or
wherein the psychiatric disorder is post traumatic stress disorder (PTSD) and the pharmaceutical composition is an SSRI, an SNRT, a cognitive enhancer, ketamine or ketamine derivative, or combinations thereof; or
wherein the psychiatric disorder is general anxiety disorder and the pharmaceutical composition is an SSRI, an SNRT, a cognitive enhancer or combinations thereof; or
wherein the psychiatric disorder is social phobia and the pharmaceutical composition is an SSRI, an SNRI, a cognitive enhancer or combinations thereof; or
wherein the psychiatric disorder is obsessive compulsive disorder and the pharmaceutical composition is an SSRI, a cognitive enhancer or combinations thereof; or
wherein the psychiatric disorder is borderline personality disorder and the pharmaceutical composition is an SSRI, an SNRI, ketamine or ketamine derivative, a cognitive enhancer or combinations thereof.

34. The method of claim 25, further comprising prescribing a treatment regimen to the subject for a disorder and wherein the treatment regimen comprises a frequency of conducting the therapy session, an absolute number of times to conduct the therapy session, and the use of a brain stimulation intervention.

35. The method of claim 25, wherein sequentially displaying each respective expression image in a plurality of expression images includes sequentially displaying each respective expression image in a plurality of expression images for a predetermined amount of time for a predetermined amount of time and wherein the predetermined amount of time is less than 10 seconds.

36. The method of claim 35, wherein the predetermined amount of time is between 0.2 seconds and 10 seconds.

37. The method of claim 25, further comprising prescribing a treatment regimen to the subject for the psychiatric disorder and wherein the prescribing comprises communicating the score to a remote server for evaluation by a prescribing clinician.

38. The method of claim 25, wherein the sequentially displaying comprises retrieving the first subset of the plurality of expression images from a database that stores the plurality of expression images, wherein the database stores, for each respective expression image in the plurality of expression images, the emotion associated with the expression image.

39. The method of claim 25, wherein the respective expression image subsets are overlapping, and wherein each subset overlaps by N−1 images with another respective image subset.

40. The method of claim 25 wherein the plurality of scores is determined as the total number of correct responses from the subject to the query as to whether the first and last expression in the respective expression image subset is the same.

41. The method of claim 40, wherein the resetting of N is based at least in part on the percentage of correct responses from the subject to the query as compared to the total number of response.

42. The method of claim 41, wherein
N is reset to N+1 when the percentage of correct responses is greater than a first threshold percentage,
N is reset to N−1 when the percentage of correct responses is less than a second threshold percentage, and
N does not reset when the percentage of correct responses is between the first and second threshold percentage.

43. The method of claim 25, wherein the one or more programs include instructions for i) conducting an initial assessment of the subject prior to the conducting the session to select the session from among a plurality of session protocols; ii) conducting an assessment of the cognitive function or emotional function of the subject after conducting the session, wherein the assessment is used as the basis, at least in part, for the prescribing a treatment regimen to the subject; or iii) providing the subject with a performance evaluation based at least in part on the plurality of scores of a plurality of sessions.

44. The method of claim 43, wherein the one or more programs include instructions for providing the subject with a performance evaluation based at least in part on the plurality of scores.

45. The method of claim 25, wherein at least one expression image in the plurality of expression images is not a facial expression.

46. The method of claim 25, wherein at least one expression image in the plurality of expression images is a facial expression.

47. The method of claim 25, wherein the predetermined intensity of the respective expression on the intensity scale of respective displayed expression images increases from the first intensity level to the second intensity level across the session, wherein the first intensity level is less than the second intensity level.

48. A method for treatment of a psychiatric disorder of a subject comprising:
i) sequentially showing each respective expression image in a plurality of expression images for a predetermined amount of time, the plurality of expression images comprising a plurality of subsets of expression images, wherein each expression image in the plurality of expression images is (a) independently associated with a respective expression in a set of expressions, (b) engineered to display or exhibit a predetermined intensity of the respective expression on an intensity scale that ranges from a first intensity level to a second intensity level of the respective expression and (c) configured to induce human amygdala activation;

ii) responsive to completion of each respective expression image subset within the plurality of expression images, receiving a response from the subject to a query as to whether the first and the last expression image in the respective expression image subset exhibits the same emotion, and wherein each respective expression image subset within the plurality of expression images consists of N expression images, wherein N is a predetermined integer;

iii) determining a score for each respective expression image subset within the plurality of expression images based at least in part upon the response to the query for the respective expression image subset; and iv) communicating the score to a remote server for evaluation by a prescribing clinician.

49. The method of claim 25, further comprising prescribing a treatment regimen to the subject for the psychiatric disorder and wherein the treatment regimen comprises the use of a pharmaceutical composition.

50. The method of claim 25, wherein the psychiatric disorder is an affective disorder (AD).

51. The method of claim 50, wherein the AD is major depressive disorder (MDD), post traumatic stress disorder (PTSD), general anxiety disorder, social phobia, obsessive compulsive disorder, treatment resistant depression, or borderline personality disorder.

52. The method of claim 48, further comprising prescribing a treatment regimen to the subject for the psychiatric disorder and wherein the treatment regimen comprises a frequency of conducting the session and an absolute number of times to conduct the session.

53. The method of claim 48, wherein the i) sequentially showing, ii) receiving, iii) determining, and iv) resetting are repeated a plurality of times in the session.

54. The method of claim 48, wherein the predetermined intensity of the respective expression on the intensity scale of respective images of a first subset of expression images in the plurality of expression images is less than the predetermined intensity of the respective expression on the intensity scale of respective images in the plurality of expression images of a second subset of expression images in the session, wherein the second subset is displayed after the first subset.

55. The method of claim 48, wherein the set of expressions comprises happy, worried, angry and sad.

56. The method of claim 51, wherein the psychiatric disorder is MDD and the pharmaceutical composition is a selective serotonin reuptake inhibitor (SSRI), a serotonin norepinephrine reuptake inhibitor (SNRT), a cognitive enhancer, ketamine or ketamine derivative, an atypical antipsychotic, a benzodiazepine, bupropion, amotrigine, lithium, a monoamine oxidase inhibitor, a tricyclic antidepressant, valproic acid, nefazodone, trazodone, pramipexole or combinations thereof; or wherein the psychiatric disorder is post traumatic stress disorder (PTSD) and the pharmaceutical composition is an SSRI, an SNRI, a cognitive enhancer, ketamine or ketamine derivative, or combinations thereof; or wherein the psychiatric disorder is general anxiety disorder and the pharmaceutical composition is an SSRI, an SNRI, a cognitive enhancer or combinations thereof; or wherein the psychiatric disorder is social phobia and the pharmaceutical composition is an SSRI, an SNRI, a cognitive enhancer or combinations thereof; or wherein the psychiatric disorder is obsessive compulsive disorder and the pharmaceutical composition is an SSRI, a cognitive enhancer or combinations thereof; or wherein the psychiatric disorder is borderline personality disorder and the pharmaceutical composition is an SSRI, an SNRI, ketamine or ketamine derivative, a cognitive enhancer or combinations thereof.

57. The method of claim 48, further comprising prescribing a treatment regimen to the subject for the psychiatric disorder and wherein the treatment regimen comprises a frequency of conducting the therapy session, an absolute number of times to conduct the therapy session, and the use of a brain stimulation intervention.

58. The method of claim 48, wherein sequentially showing each respective expression image in a plurality of expression images includes sequentially showing each respective expression image in a plurality of expression images for a predetermined amount of time for a predetermined amount of time and wherein the predetermined amount of time is less than 10 seconds.

59. The method of claim 48, wherein the predetermined amount of time is between 0.2 seconds and 10 seconds.

60. The method of claim 48, further comprising prescribing a treatment regimen to the subject for the psychiatric disorder and wherein the prescribing comprises communicating the score to a remote server for evaluation by a prescribing clinician.

61. The method of claim 48, wherein the sequentially showing comprises retrieving the first subset of the plurality of expression images from a database that stores the plurality of expression images, wherein the database stores, for each respective expression image in the plurality of expression images, the emotion associated with the expression image.

62. The method of claim 48, wherein the respective expression image subsets are overlapping, and wherein each subset overlaps by N−1 images with another respective image subset.

63. The method of claim 48 wherein the plurality of scores is determined as the total number of correct responses from the subject to the query as to whether the first and last expression in the respective expression image subset is the same.

64. The method of claim 63, wherein the resetting of N is based at least in part on the percentage of correct responses from the subject to the query as compared to the total number of response.

65. The method of claim 64, wherein

N is reset to N+1 when the percentage of correct responses is greater than a first threshold percentage, N is reset to N−1 when the percentage of correct responses is less than a second threshold percentage, and N does not reset when the percentage of correct responses is between the first and second threshold percentage.

66. The method of claim 48, wherein the one or more programs include instructions for i) conducting an initial assessment of the subject prior to the conducting the session to select the session from among a plurality of session protocols; ii) conducting an assessment of the cognitive function or emotional function of the subject after conducting the session, wherein the assessment is used as the basis, at least in part, for the prescribing a treatment regimen to the subject; or iii) providing the subject with a performance evaluation based at least in part on the plurality of scores of a plurality of sessions.

67. The method of claim 66, wherein the one or more programs include instructions for providing the subject with a performance evaluation based at least in part on the plurality of scores.

68. The method of claim 48, wherein at least one expression image in the plurality of expression images is not a facial expression.

69. The method of claim 48, wherein at least one expression image in the plurality of expression images is a facial expression.

70. The method of claim 48 wherein the predetermined intensity of the respective expression on the intensity scale of respective displayed expression images increases from the first intensity level to the second intensity level across the session, wherein the first intensity level is less than the second intensity level.

* * * * *